US010066220B2

(12) United States Patent
Hansen et al.

(10) Patent No.: US 10,066,220 B2
(45) Date of Patent: Sep. 4, 2018

(54) POLYPEPTIDES HAVING ORGANOPHOSPHOROUS HYDROLASE ACTIVITY

(71) Applicant: NOVOZYMES A/S, Bagsvaerd (DK)

(72) Inventors: Bjarne Gram Hansen, Bagsvaerd (DK); Steffen Danielsen, Bagsvaerd (DK); Lars Kobberoee Skov, Bagsvaerd (DK); Leonardo De Maria, Bagsvaerd (DK); Julie Bille Rannes, Bagsvaerd (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 15/342,856

(22) Filed: Nov. 3, 2016

(65) Prior Publication Data

US 2017/0073653 A1 Mar. 16, 2017

Related U.S. Application Data

(62) Division of application No. 14/403,949, filed as application No. PCT/EP2013/061314 on May 31, 2013, now Pat. No. 9,512,413.

(60) Provisional application No. 61/656,190, filed on Jun. 6, 2012.

(30) Foreign Application Priority Data

May 31, 2012 (EP) .................................... 12170369

(51) Int. Cl.

| | |
|---|---|
| ***A62D 3/02*** | (2007.01) |
| ***A62D 101/02*** | (2007.01) |
| ***A62D 101/04*** | (2007.01) |
| ***C12N 9/16*** | (2006.01) |
| ***A62D 3/30*** | (2007.01) |
| *A62D 101/26* | (2007.01) |

(52) U.S. Cl.

CPC ................ *C12N 9/16* (2013.01); *A62D 3/02* (2013.01); *A62D 3/30* (2013.01); *C12Y 301/08002* (2013.01); *A62D 2101/02* (2013.01); *A62D 2101/04* (2013.01); *A62D 2101/26* (2013.01)

(58) Field of Classification Search

None

See application file for complete search history.

(56) References Cited

U.S. PATENT DOCUMENTS

| | | | |
|---|---|---|---|
| 8,709,773 | B2 | 4/2014 | Danielsen |
| 2010/0124769 | A1 | 5/2010 | Brown |
| 2010/0281582 | A1 | 11/2010 | Brown |
| 2015/0004655 | A1 | 1/2015 | Woglis |

FOREIGN PATENT DOCUMENTS

| | | | |
|---|---|---|---|
| WO | 98/08940 | A1 | 3/1998 |
| WO | 99/43791 | A2 | 9/1999 |
| WO | 2008/151043 | A1 | 12/2008 |
| WO | 2009/130285 | A1 | 10/2009 |
| WO | 2010/088387 | A1 | 8/2010 |
| WO | 2010/088463 | A2 | 8/2010 |
| WO | 2010/128115 | A | 11/2010 |
| WO | 2010/128116 | A1 | 11/2010 |
| WO | 2012/018691 | A2 | 2/2012 |
| WO | 2012/044836 | A1 | 4/2012 |
| WO | 2012/125937 | A2 | 9/2012 |

OTHER PUBLICATIONS

UniProt Database Accession No. F7AMF2, May 2012, 2 pages (Year: 2012).*
GenBank Accession No. AK173872, Jul. 2008, 1 page (Year: 2008).*
Scanlan et al., "Evolution in action", Chem. Biol. 2:71-75, 1995 (Year: 1995).*
Anonymous, 2012, Uniprot No. XP002713789.
Anonymous, 2008, Uniprot accession No. UPI000180B9A5.
Birren et al, 2012—Uniprot Access No. H2Y755.
Rastogi et al, 1997, Biochem Biaphys Res Comm 241, 294-296.

* cited by examiner

*Primary Examiner* — David Steadman
(74) *Attorney, Agent, or Firm* — Robert Starnes

(57) ABSTRACT

The present invention relates to isolated polypeptides having organophosphorous hydrolase activity, and polynucleotides encoding the polypeptides. The invention also relates to nucleic acid constructs, vectors, and host cells comprising the polynucleotides as well as methods of producing and using the polypeptides.

12 Claims, No Drawings

Specification includes a Sequence Listing.

POLYPEPTIDES HAVING ORGANOPHOSPHOROUS HYDROLASE ACTIVITY

CROSS-REFERENCE TO RELATED APPLICATIONS

This application is a divisional application of U.S. application Ser. No. 14/403,949 filed Nov. 25, 2014, and issued on Dec. 6, 2016 as U.S. Pat. No 9,512,413, which is a 35 U.S.C. 371 national application of PCT/EP2013/061314, filed May 30, 2013, which claims priority or the benefit under 35 U.S.C. 119 of European application no. 12170369.8, filed May 31, 2012 and U.S. provisional application No. 61/656,190, filed Jun. 6, 2012, the contents of which are fully incorporated herein by reference.

REFERENCE TO A SEQUENCE LISTING

This application contains a Sequence Listing in computer readable form, which is incorporated herein by reference.

BACKGROUND

Field of the Invention

The present invention relates to polypeptides having organophosphorous hydrolase activity, and polynucleotides encoding the polypeptides. The invention also relates to nucleic acid constructs, vectors, and host cells comprising the polynucleotides as well as methods of producing and using the polypeptides.

Description of the Related Art

Organophosphorous compounds are known in the art. In particular some warfare agents are known to be organophosphorous compounds such as the G-type nerve agents such as Sarin, Cyclosarin, and Soman and the V-type nerve agents such as VX. Other organophosphorous compounds are known as pesticides.

It is desirable to be able to decontaminate areas contaminated with such organophosphorous compounds. A polypeptide having organophosphorous hydrolase activity, such as diisopropylfluorophosphatase activity has been suggested for this purpose since such polypeptides are capable of hydrolyzing harmful organophosphorous compounds and thereby converting them to less harmful products.

In WO 99/43791, a diisopropylfluorophosphatase from *Loligo vulgaris* is disclosed and its potential use for decontamination among other applications is also described.

WO 2009/130285, WO 2010/128115 and WO 2010/128116 disclose other diisopropylfluorophosphatases from *Pseudoalteramonas haloplanktis, Octopus vulgaris*, and *Aplysia californica.*

It is an object of the present invention to provide polypeptides having organophosphorous hydrolase e.g. diisopropylfluorophosphatase activity and polynucleotides encoding the polypeptides, in particular having high stability and/or high specific activity.

SUMMARY OF THE INVENTION

The present invention relates to isolated polypeptides having organophosphorous hydrolase activity selected from the group consisting of:

(a) a polypeptide having at least 65% sequence identity to the mature polypeptide of SEQ ID NO: 2, SEQ ID NO: 4, SEQ ID NO: 6, or SEQ ID NO: 8;

(b) a polypeptide encoded by a polynucleotide that hybridizes under medium stringency conditions with (i) the mature polypeptide coding sequence of SEQ ID NO: 1, SEQ ID NO: 3, SEQ ID NO: 5, or SEQ ID NO: 7, or (ii) the full-length complement of (i);

(c) a polypeptide encoded by a polynucleotide having at least 65% sequence identity to the mature polypeptide coding sequence of SEQ ID NO: 1, SEQ ID NO: 3, SEQ ID NO: 5, or SEQ ID NO: 7;

(d) a variant of the mature polypeptide of SEQ ID NO: 2, SEQ ID NO: 4, SEQ ID NO: 6, or SEQ ID NO: 8, comprising a substitution, deletion, and/or insertion at one or more (e.g., several) positions; and (e) a fragment of the polypeptide of (a), (b), (c), or (d) that has organophosphorous hydrolase activity.

The present invention also relates to isolated polynucleotides encoding the polypeptides of the present invention; nucleic acid constructs; recombinant expression vectors; recombinant host cells comprising the polynucleotides; and methods of producing the polypeptides.

The present invention also relates to methods for removing an organophosphorous compound, comprising contacting the organophosphorous compound with a polypeptide of the invention.

DEFINITIONS

Organophosphorous hydrolase: The term "organophosphorous hydrolase" is defined herein as hydrolytic activity to organophosphorous compounds, in particular phosphorous anhydride bonds in organophosphorous compounds including nerve gases. Thus the term includes an enzyme with hydrolase activity and/or esterase activity, e.g. organophosphorous hydrolase activity (such as an organophosphoesterase activity) or organophosphoric acid anhydrolase (OPAA) activity, or carboxylesterase activity, diisopropylfluorophosphatase (DFPase) activity (EC 3.1.8.2), dehalogenase activity, catalyzing the hydrolyses of phosphorus-sulfur bonds, prolidase activity and/or imidodipeptidase activity.

The term "DFPase (EC3.1.8.2)" is defined herein as diisopropylfluorophosphatase, dialkylfluorophosphatase, diisopropylphosphorofluoridate hydrolase, diisopropylfluorophosphonate dehalogenase, diisopropylphosphofluoridase, isopropylphosphorofluoridase, organophosphate acid anhydrase, organophosphorous acid anhydrolase, somanase, tabunase. DFPases acts on phosphorus anhydride bonds (such as phosphorus-halide and phosphorus-cyanide) in organophosphorous compounds (including nerve gases).

For purposes of the present invention, organophosphorous hydrolase activity is determined according to the procedure described in Example 3. In one aspect, the polypeptides of the present invention have at least 20%, e.g., at least 40%, at least 50%, at least 60%, at least 70%, at least 80%, at least 90%, at least 95%, or at least 100% of the organophosphorous hydrolase activity of the mature polypeptide of SEQ ID NO: 2, SEQ ID NO: 4, SEQ ID NO: 6, or SEQ ID NO: 8.

Decontamination: The term "decontamination" is to be understood herein as removing harmful agents such as organophosphorous compounds, e.g. nerve gases, toxins, pesticides, thus the term includes e.g. detoxification activity.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic domain having one or more (e.g., several) amino acids absent from the amino and/or carboxyl terminus of a mature polypeptide or domain; wherein the fragment has organophosphorous hydrolase activity. In one aspect, a fragment contains at least 302 amino acid residues (e.g., amino acids 12 to 314 of SEQ ID NO: 2, or amino acids 7 to 309 of SEQ ID NO: 4).

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having organophosphorous hydrolase activity.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment–Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having organophosphorous hydrolase activity. In one aspect, a subsequence contains at least 906 nucleotides (e.g., nucleotides 34 to 942 of SEQ ID NO: 1, or nucleotides 19 to 927 of SEQ ID NO: 3).

Variant: The term "variant" means a polypeptide having organophosphorous hydrolase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

DETAILED DESCRIPTION

Polypeptides Having Organophosphorous Hydrolase Activity

In an embodiment, the present invention relates to isolated polypeptides having a sequence identity to the mature polypeptide of SEQ ID NO: 2, SEQ ID NO: 4, SEQ ID NO: 6, or SEQ ID NO: 8 of at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have organophosphorous hydrolase activity. In one aspect, the polypeptides differ by no more than 10 amino acids, e.g., 1, 2, 3, 4, 5, 6, 7, 8, or 9, from the mature polypeptide of SEQ ID NO: 2, SEQ ID NO: 4, SEQ ID NO: 6, or SEQ ID NO: 8.

A polypeptide of the present invention preferably comprises or consists of the amino acid sequence of SEQ ID NO: 2, SEQ ID NO: 4, SEQ ID NO: 6, or SEQ ID NO: 8; or SEQ ID NO: 9 to SEQ ID NO: 26; or SEQ ID NO: 27 to SEQ ID NO: 31; or an allelic variant thereof; or is a fragment thereof having organophosphorous hydrolase activity. In another aspect, the polypeptide comprises or consists of the mature polypeptide of SEQ ID NO: 2, SEQ ID NO: 4, SEQ ID NO: 6, or SEQ ID NO: 8; or SEQ ID NO: 9 to SEQ ID NO: 26; or SEQ ID NO: 27 to SEQ ID NO: 31.

In another embodiment, the present invention relates to an isolated polypeptide having organophosphorous hydrolase activity encoded by a polynucleotide that hybridizes under medium stringency conditions, medium-high stringency conditions, high stringency conditions, or very high stringency conditions with (i) the mature polypeptide coding sequence of SEQ ID NO: 1, SEQ ID NO: 3, SEQ ID NO: 5, or SEQ ID NO: 7, or (ii) the full-length complement of (i) (Sambrook et al., 1989, *Molecular Cloning, A Laboratory Manual,* 2d edition, Cold Spring Harbor, New York).

The polynucleotide of SEQ ID NO: 1, SEQ ID NO: 3, SEQ ID NO: 5, or SEQ ID NO: 7, or a subsequence thereof, as well as the polypeptide of SEQ ID NO: 2, SEQ ID NO: 4, SEQ ID NO: 6, or SEQ ID NO: 8, or a fragment thereof, may be used to design nucleic acid probes to identify and clone DNA encoding polypeptides having organophosphorous hydrolase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having organophosphorous hydrolase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 3, SEQ ID NO: 5, or SEQ ID NO: 7, or a subsequence thereof, the carrier material is used in a Southern blot.

For purposes of the present invention, hybridization indicates that the polynucleotide hybridizes to a labeled nucleic acid probe corresponding to (i) SEQ ID NO: 1, SEQ ID NO: 3, SEQ ID NO: 5, or SEQ ID NO: 7; (ii) the mature polypeptide coding sequence of SEQ ID NO: 1, SEQ ID NO: 3, SEQ ID NO: 5, or SEQ ID NO: 7; (iii) the full-length complement thereof; or (iv) a subsequence thereof; under medium to very high stringency conditions. Molecules to which the nucleic acid probe hybridizes under these conditions can be detected using, for example, X-ray film or any other detection means known in the art.

In another embodiment, the present invention relates to an isolated polypeptide having organophosphorous hydrolase activity encoded by a polynucleotide having a sequence identity to the mature polypeptide coding sequence of SEQ ID NO: 1, SEQ ID NO: 3, SEQ ID NO: 5, or SEQ ID NO: 7 of at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2, SEQ ID NO: 4, SEQ ID NO: 6, or SEQ ID NO: 8, comprising a substitution, deletion, and/or insertion at one or more (e.g., several) positions. In an embodiment, the number of amino acid substitutions, deletions and/or insertions introduced into the mature polypeptide of SEQ ID NO: 2, SEQ ID NO: 4, SEQ ID NO: 6, or SEQ ID NO: 8 is not more than 10, e.g., 1, 2, 3, 4, 5, 6, 7, 8 or 9. Preferably, the substitution, deletion, and/or insertion are only substitutions. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for organophosphorous hydrolase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

In an embodiment, essential amino acids in the amino acid sequence of SEQ ID NO: 2 are located at positions E25, N132, N190, and D239. Other essential positions in SEQ ID NO: 2 may be N133, T204, S282, N283, and H298.

In another embodiment, essential amino acids in the amino acid sequence of SEQ ID NO: 4 are located at positions E20, N127, N185, and D234. Other essential positions in SEQ ID NO: 4 may be N128, T199, S277, N278, and H293.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World,* 4: 35-48.

Sources of Polypeptides Having Organophosphorous Hydrolase Activity

A polypeptide having organophosphorous hydrolase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a Phlebobranchia (a suborder of sea squirts in the order Enterogona) polypeptide. Preferably, it is a Cionidae polypeptide; for example, the polypeptide may be a *Ciona* polypeptide such as a *Ciona edwardsi, Ciona fascicularis, Ciona gelatinosa, Ciona imperfect, Ciona intestinalis, Ciona mollis*, or *Ciona savignyi* polypeptide.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from the above sources, or DNA samples obtained using the above-mentioned probes. Techniques for isolating DNA directly from natural habitats are well known in the art. A polynucleotide encoding the polypeptide may then be obtained by similarly screening a genomic DNA or cDNA library. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Ciona*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, SEQ ID NO: 3, SEQ ID NO: 5, or SEQ ID NO: 7, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (*Praha*) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In, Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium*

*bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In a preferred aspect, the cell is a *Ciona* cell. In a more preferred aspect, the cell is a *Ciona savignyi* or *Ciona intestinalis* cell.

The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana.*

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Compositions

The present invention also relates to compositions comprising a polypeptide of the present invention. The compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having organophosphorous hydrolase activity (organophosphorous hydrolases), or compositions thereof.

In one preferred embodiment the invention also directed to the use of organophosphorous hydrolases of the invention for decontaminating an area or a device contaminated with at least one harmful or undesired organophosphorous compound. The organophosphorous hydrolases of the invention or a composition comprising the organophosphorous hydrolases of the invention is applied to the area or the device in an amount sufficient to degrade at least part of at least one harmful or undesired organophosphorous compound.

In another embodiment the organophosphorous hydrolases of the invention may be used emulsions such as micro emulsions for applying to e.g. a human or animals. The organophosphorous hydrolases of the invention or a composition comprising the organophosphorous hydrolases of the invention is applied to the human or animal to protect against at least one harmful or undesired organophosphorous compound.

In a further embodiment the organophosphorous hydrolases of the invention may be incorporated in an assay for detection of at least one harmful or undesired organophosphorous compound. Such assays could be beneficial for quick assessment of the presence of undesired organophosphorous compound Harmful or undesired organophosphorous compounds includes toxic organophosphorous cholinesterase-inhibiting compounds including nerve gases (G agents or G-series) such as ethyl N,N-dimethylphosphoramidocyanidate (tabun), diisopropylfluorophosphate (DFP), O-isopropyl methylphosphonofluoridate (sarin), O-pinacolyl methyl phosphonofluoridate (soman) and O-cyclohexyl methylphosphonofluoridate.

Other harmful compounds includes V agents (or V-series), which may comprise VX, VE, VG, VM, VR Tetriso and Soviet V-gas (Russian VX).

The pesticides may comprise fungicides, insecticides, herbicide and rodenticides. The pesticide may be Demeton-S, Demeton-S-methyl, Demeton-S-methylsulphon, Demeton-methyl, Parathion, Phosmet, Carbophenothion, Benoxafos, Azinphos-methyl, Azinphos-ethyl, Amiton, Amidithion, Cyanthoate, Dialiphos, Dimethoate, Dioxathion, Disulfoton, Endothion, Etion, Ethoate-methyl, Formothion, Malathion, Mercarbam, Omethoate, Oxydeprofos, Oxydisulfoton, Phenkapton, Phorate, Phosalone, Prothidathion, Prothoate, Sophamide, Thiometon, Vamidothion, Methamidophos.

The present invention is further described by the following examples that should not be construed as limiting the scope of the invention.

EXAMPLES

Chemicals used as buffers and substrates were commercial products of at least reagent grade.

Example 1

Cloning and Expression of Organophosphorous Hydrolase Gene

Cloning

Synthetic genes encoding the His-tagged organophosphorous hydrolases from *Ciona savigny* (CSAV) (SEQ ID NO: 6) and *Ciona intestinalis* (CINT) (SEQ ID NO: 8) were designed and the genes were synthesized by a commercial supplier. Subsequently an expression construct for expression of the organophosphorous hydrolases was created using standard methods of molecular biology (Sambrook et al. (1989); Ausubel et al. (1995); Harwood and Cutting (1990) and this was integrated by homologous recombination into a *Bacillus subtilis* host cell genome. The gene construct was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including the mRNA stabilizing sequence. The gene coding for Chloramphenicol acetyl-transferase was used as marker.

Cloning of Variants of *Ciona Savigny* DFPase 17 variants containing the following single amino acid changes in the *Ciona savigny* DFPase (SEQ ID NO: 6) were cloned and expressed: M63A (SEQ ID NO: 9), M63G (SEQ ID NO: 10), R107I (SEQ ID NO: 11), R107V (SEQ ID NO: 12), R107L (SEQ ID NO: 13), A109S (SEQ ID NO: 14), A109C (SEQ ID NO: 15), E178F (SEQ ID NO: 16), E178I (SEQ ID NO: 17), E178L (SEQ ID NO: 18), E178V (SEQ ID NO: 19), R180F (SEQ ID NO: 20), R180I (SEQ ID NO: 21), R180L (SEQ ID NO: 22), R180V (SEQ ID NO: 23), R180M (SEQ ID NO: 24), Y276H (SEQ ID NO: 25), and Y276F (SEQ ID NO: 26).

Cloning of Variants of *Ciona Intestinalis* DFPase 5 variants containing the following single amino acid changes in the *Ciona intestinalis* DFPase (SEQ ID NO: 8) were cloned and expressed: E173F (SEQ ID NO: 27), E173V (SEQ ID NO: 28), R175A (SEQ ID NO: 29), S60L (SEQ ID NO: 30), and S60R (SEQ ID NO: 31).

Cloning of Variants of CSAV and CINT DFPases

To generate variants of SEQ ID NO: 6 and SEQ ID NO: 8, PCR-based site-directed mutagenesis was done with a mutagenic primer (see Table 1) that introduce the desired sequence change (substitutions). Primers were designed so that the mutation lies in the middle of the oligonucleotide with sufficient flanking nucleotides (15-25). The *Bacillus* genomic DNA with CSAV DFPase and CINT DFPase was used as template and PCR was setup with a proofreading DNA polymerase (Phusion DNA polymerase (New England Biolabs). Subsequently, an expression construct for expression of the organophosphorous hydrolases were created using standard methods of molecular biology (Sambrook et al. (1989); Ausubel et al. (1995); Harwood and Cutting (1990) and this was integrated by homologous recombination into a *Bacillus subtilis* host cell genome. The gene construct was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including the mRNA stabilizing sequence. The gene coding for Chloramphenicol acetyl-transferase was used as marker. Correct sequences were verified by sequencing colony PCR products from *Bacillus subtilis* transformants.

TABLE 1

Mutagenic primers used for PCR-based site-directed mutagenesis of *Ciona savigny* DFPase. Bold letters represent sites of directed mutagenesis.

| Mutation | SEQ ID NO. | Mutagenic primer |
|---|---|---|
| M63A | 32 | 5'-CGGTTCTCGTCCGCAGCCTC**AGC**AGGCGCAACCGCATAGAAGCG-3' |
| M63G | 33 | 5'-CGGTTCTCGTCCGCAGCCTC**ACC**AGGCGCAACCGCATAGAAGCG-3' |
| R107I | 34 | 5'-GGTCTGATTGACAACCAGCAGG**GAT**ACCTCCATAGCCGTCAAAATGAG-3' |
| R107V | 35 | 5'-GGTCTGATTGACAACCAGCAGG**AAC**ACCTCCATAGCCGTCAAAATGAG-3' |
| R107L | 36 | 5'-GGTCTGATTGACAACCAGCAGG**AAG**ACCTCCATAGCCGTCAAAATGAG-3' |
| A109S | 37 | 5'-CCTCATGGTCTGATTGACAACC**TGA**AGGGCGACCTCCATAGCCGTC-3' |
| A109C | 38 | 5'-CCTCATGGTCTGATTGACAACC**ACA**AGGGCGACCTCCATAGCCGTC-3' |
| E178F | 39 | 5'-CAGTAAAGATAGTCTCGCGGTC**AAA**AGGTGAAGGTGCGATAGGTGATC-3' |
| E178I | 40 | 5'-CAGTAAAGATAGTCTCGCGGTC**GAT**AGGTGAAGGTGCGATAGGTGATC-3' |
| E178L | 41 | 5'-CAGTAAAGATAGTCTCGCGGTC**AAG**AGGTGAAGGTGCGATAGGTGATC-3' |
| E178V | 42 | 5'-CAGTAAAGATAGTCTCGCGGTC**AAC**AGGTGAAGGTGCGATAGGTGATC-3' |
| R180F | 43 | 5'-GAAGGCTCAGTAAAGATAGTCTC**AAA**GTCCTCAGGTGAAGGTGCGATAG-3' |
| R180I | 44 | 5'-GAAGGCTCAGTAAAGATAGTCTC**GAT**GTCCTCAGGTGAAGGTGCGATAG-3' |
| R180L | 45 | 5'-GAAGGCTCAGTAAAGATAGTCTC**AAG**GTCCTCAGGTGAAGGTGCGATAG-3' |
| R180V | 46 | 5'-GAAGGCTCAGTAAAGATAGTCTC**AAC**GTCCTCAGGTGAAGGTGCGATAG-3' |
| R180M | 47 | 5'-GAAGGCTCAGTAAAGATAGTCTC**CAT**GTCCTCAGGTGAAGGTGCGATAG-3' |
| Y276H | 48 | 5'-GATATACCTCGATGTGTGAAGCGCC**GTG**GTTAGCAACAAGAAGGCGACCAG-3' |
| Y276F | 49 | 5'-GATATACCTCGATGTGTGAAGCGCC**AAA**GTTAGCAACAAGAAGGCGACCAG-3' |

TABLE 2

Primers used for PCR-based site-directed mutagenesis of *Ciona intestinalis* DFPase. Bold letters represent sites of directed mutagenesis.

| Mutation | SEQ ID NO. | Mutagenic primer |
|---|---|---|
| E173F | 50 | 5'-GAAGATCGTCGTGCGGTC**GAA**TACTGAAGGAGCAACAGGTGAG-3' |
| E173V | 51 | 5'-GAAGATCGTCGTGCGGTC**AAC**TACTGAAGGAGCAACAGGTGAG-3' |
| R175A | 52 | 5'-CTCCGCGAAGATCGTCGT**AGC**GTCCTCTACTGAAGGAGCAACAG-3' |
| S60L | 53 | 5'-CTCGCGGTTGTCGTCAGC**AAG**CTCCATAGGAGCTACTGCATAG-3' |
| S60R | 54 | 5'-CTCGCGGTTGTCGTCAGC**GCG**CTCCATAGGAGCTACTGCATAG-3' |

Organophosphorous Hydrolase Expression

Chloramphenicol resistant *Bacillus subtilis* transformants harboring the His-tagged organophosphorous hydrolase genes described above were inoculated into 100 ml growth medium in 250 ml Erlenmeyer flasks. Cultures were grown for 3 days at 30° C. and 250 rpm.

Example 2

Purification

Cells were harvested from the cultures by centrifugation at 5000 rpm for 15 min and supernatants filtered through a 0.22 μm bottle top filter (Nalgene). Solid MES and imidazole were added to the following concentrations: 10 mM imidazole and 0.5 mM MES. pH was adjusted to 7.6 and the solution purified using a chelating sepharose FF column preloaded with $Cu^{2+}$ on a Äkta Explorer system. Elution was performed step-wise with increasing imidazole concentrations (0%-100% of 500 mM imidazole).

Fractions belonging to the same peak were pooled, concentrated and buffer-exchanged into 50 mM TRIS pH 7.0 using Amicon Ultra centrifugal filter devices with a 10 kDa cut-off.

Example 3

Measurement of Organophosphorous Hydrolase Activity

Organophosphorous Hydrolase Activity

The organophosphorous hydrolase activity of the *Ciona savigny* DFPase was determined either by a pH stat assay as described in Blum et al., *JACS,* 128 (2006): 12750-12757, or using in situ Fourier transform infrared spectroscopy as described in Gäb et al., *Anal Biochem,* 385 (2009):187-193. In the pH stat assay DFP hydrolysis was determined by a measuring the release of fluoride ions at 298 K in a nitrogen atmosphere. The assay was performed in 3 ml at pH 7.5, containing 10 mM NaCl and 10% acetonitrile. The reaction was initiated by addition of 2 microliter of 0.5 mg/ml organophosphorous hydrolase. Initial velocities were determined at eight different substrate concentrations (0.5-10 mM), and corrected for the uncatalyzed rate of DFP hydrolysis. In situ Fourier transform infrared (FTIR) spectroscopy was used to measure real-time reaction rates of the nerve agent substrates when these were hydrolyzed to the corresponding phosphoric and phosphonic acids.

Hydrolysis of dihydrocoumarine was followed at 25° C. at 235 nm in a spectrophotometer by addition of purified organophosphorous hydrolase to a solution containing 1 mM dihydrocoumarine in 50 mM Tris, 2 mM $CaCl_2$, pH 7.5. The specific activities of hydrolysis of dihydrocoumarine for the organophosphorous hydrolases when calculated as decrease in absorbance at 235 nm per minute per mg of protein was calculated to be: 3 U/mg for *Ciona savigny.*

Activity Tests

The organophosphorous hydrolases were tested with the following G-agents: DFP, Soman, Cyclosarin and Sarin. The *Ciona savigny* organophosphorous hydrolase showed activity against all four G-agents.

TABLE 3

Specific activities. One U is defined as the hydrolysis of 1 μmol substrate per minute.

| Substrate | Specific activity of *Ciona savigny* organophosphorous hydrolase in U/mg |
|---|---|
| DFP (1.79%) | 118 |
| Sarin (1.97%) | 101 |
| Soman (1.89%) | 48 |
| Cyclosarin (1.9%) | 75 |
| Coumarine | 3 |

The enzymatic activities of *Ciona savigny* and *Ciona intestinalis* organophosphorous hydrolase towards Soman and VX were also performed using NMR spectroscopy. Experiments were performed in 50 mM TRIS buffer, 2 mM $CaCl_2$, 20% $D_2O$ pH 7.0. The specific activities of hydrolysis of Soman for the organophosphorous hydrolases were calculated from standard curves for the Soman break-down product pinacolyl methylphosphonic acid (PMPA). The specific activities of hydrolysis of VX for the organophosphorous hydrolases were calculated from standard curves for the VX break-down product ethyl methylphosphonic acid (EMPA).

TABLE 4

Specific activity. One U is defined as the hydrolysis of 1 μmol substrate per minute.

| Substrate | Specific activity of *Ciona intestinalis* organophosphorous hydrolase in U/mg |
|---|---|
| Soman | 25.5 |
| VX | 0.012 |

TABLE 5

Specific activity. One U is defined as the hydrolysis of 1 μmol substrate per minute.

| Substrate | Specific activity of *Ciona savigny* organophosphorous hydrolase in U/mg |
|---|---|
| Soman | 17.8 |
| VX | 0.017 |

VX-hydrolysis of the organophosphorous hydrolases were determined in a colorimetric assay based on the detection of free thiols with DTNB (5,5'-dithiobis-2-nitrobenzoate), as described in Broomfield et al., CBMTS III Conference Proceedings, Spietz, Switzerland, May 7-12 (2000).

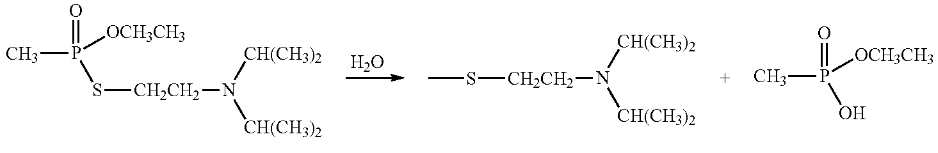

VX

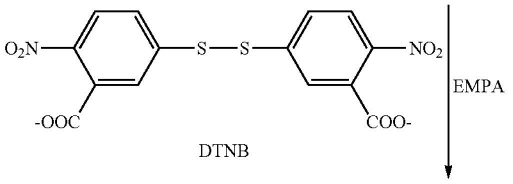

DTNB

-continued

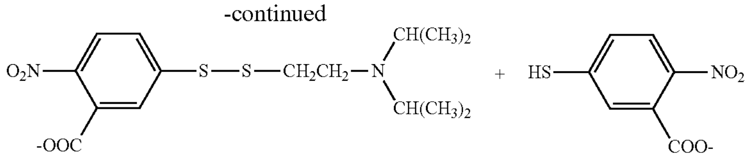

5-thio, 2-nitro benzoic acid
(yellow chromophore)

Principle of DTNB assay for detection of organophosphorous hydrolase catalysed VX breakdown.

In the DTNB assay the organophosphorous hydrolase catalyzed VX hydrolysis is measured as the accumulation of 5-thio, 2-nitro bisbenzoate at 412 nm. The assay was performed in 200 μl at pH 7.0, containing 50 mM TRIS buffer, 2 mM $CaCl_2$, 0.2 mM DTNB and 3.4 mM VX and 30 μg organophosphorous hydrolase enzyme (*Ciona intestinalis* organophosphorous hydrolase or *Ciona savigny* organophosphorous hydrolase).

VX hydrolysis of all variants of CI NT and CSAV DFPases were measured. The results in Tables 6 and 7 are the average of three independent replicates.

TABLE 6

Relative VX breakdown activity of *Ciona savigny* DFPase variants. Measured as the accumulation of 5-thio, 2-nitro bisbenzoate at 412 nm. 30 μg of CSAV DFPase enzyme was used in each assay.

| Mutation | SEQ ID NO. | Relative activity compared to CSAV DFPase activity |
|---|---|---|
| wildtype | 2 | 1.0 |
| M63A | 9 | 0.7 |
| M63G | 10 | 0.8 |
| R107I | 11 | 0.5 |
| R107V | 12 | 0.8 |
| R107L | 13 | 0.6 |
| A109S | 14 | 0.4 |
| A109C | 15 | 0.7 |
| E178F | 16 | 0.7 |
| E178I | 17 | 0.8 |
| E178L | 18 | 0.7 |
| E178V | 19 | 0.8 |
| R180F | 20 | 0.9 |
| R180I | 21 | 1.8 |
| R180L | 22 | 1.4 |
| R180V | 23 | 0.4 |
| R180M | 24 | 1.0 |

TABLE 6-continued

Relative VX breakdown activity of *Ciona savigny* DFPase variants. Measured as the accumulation of 5-thio, 2-nitro bisbenzoate at 412 nm. 30 μg of CSAV DFPase enzyme was used in each assay.

| Mutation | SEQ ID NO. | Relative activity compared to CSAV DFPase activity |
|---|---|---|
| Y276H | 25 | 0.6 |
| Y276F | 26 | 0.5 |

TABLE 7

Relative VX breakdown activity of *Ciona intestinalis* DFPase variants. Measured as the accumulation of 5-thio, 2-nitro bisbenzoate at 412 nm. 30 μg of CINT DFPase enzyme was used in each assay.

| Mutation | SEQ ID NO. | Relative activity compared to CINT DFPase activity |
|---|---|---|
| wildtype | 4 | 1.0 |
| E173F | 27 | 0.4 |
| E173V | 28 | 0.6 |
| R175A | 29 | 0.9 |
| S60L | 30 | 1.2 |
| S60R | 31 | 0.4 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A method for removing an organophosphorous compound, comprising contacting the organophosphorous compound with a polypeptide having organophosphorous hydrolase activity and comprising an amino acid sequence having at least 90% sequence identity to the amino acid sequence of amino acids 7 to 309 of SEQ ID NO: 4 to remove the organophosphorous compound.

2. The method of claim 1, wherein the polypeptide has at least 94% sequence identity to the amino acid sequence of amino acids 7 to 309 of SEQ ID NO: 4.

3. The method of claim 1, wherein the polypeptide has at least 95% sequence identity to the amino acid sequence of amino acids 7 to 309 of SEQ ID NO: 4.

4. The method of claim 1, wherein the polypeptide has at least 96% sequence identity to the amino acid sequence of amino acids 7 to 309 of SEQ ID NO: 4.

5. The method of claim 1, wherein the polypeptide has at least 99% sequence identity to the amino acid sequence of amino acids 7 to 309 of SEQ ID NO: 4.

6. The method of claim 1, wherein the organophosphorous compound is a nerve gas, toxin or pesticide.

7. The method of claim 1, wherein the polypeptide has at least 91% sequence identity to the amino acid sequence of amino acids 7 to 309 of SEQ ID NO: 4.

8. The method of claim 1, wherein the polypeptide has at least 92% sequence identity to the amino acid sequence of amino acids 7 to 309 of SEQ ID NO: 4.

9. The method of claim 1, wherein the polypeptide has at least 93% sequence identity to the amino acid sequence of amino acids 7 to 309 of SEQ ID NO: 4.

10. The method of claim 1, wherein the polypeptide has at least 97% sequence identity to the amino acid sequence of amino acids 7 to 309 of SEQ ID NO: 4.

11. The method of claim 1, wherein the polypeptide has at least 98% sequence identity to the amino acid sequence of amino acids 7 to 309 of SEQ ID NO: 4.

12. The method of claim 1, wherein the polypeptide comprises the amino acid sequence of amino acids 7 to 309 of SEQ ID NO: 4.

* * * * *

SEQUENCE LISTING

```
<160> NUMBER OF SEQ ID NOS: 54

<210> SEQ ID NO 1
<211> LENGTH: 966
<212> TYPE: DNA
<213> ORGANISM: Ciona savignyi
<220> FEATURE:
<221> NAME/KEY: CDS
<222> LOCATION: (1)..(963)

<400> SEQUENCE: 1

atg gca gac tca gga atc cct gtt atc aaa gag cct caa ttc aca atg       48
Met Ala Asp Ser Gly Ile Pro Val Ile Lys Glu Pro Gln Phe Thr Met
1               5                   10                  15

atc act aaa gac atc aac ggc tca gaa ggc cct gtt ttc gac aca aaa       96
```

-continued

```
Ile Thr Lys Asp Ile Asn Gly Ser Glu Gly Pro Val Phe Asp Thr Lys
            20                  25                  30

ggt cgc ttc tat gcg gtt gcg cct atg gag gct gcg gac gag aac cgc      144
Gly Arg Phe Tyr Ala Val Ala Pro Met Glu Ala Ala Asp Glu Asn Arg
        35                  40                  45

gag cct ggt cag ttt act gac ggc atc gca gga aaa ctt tac caa gtt      192
Glu Pro Gly Gln Phe Thr Asp Gly Ile Ala Gly Lys Leu Tyr Gln Val
    50                  55                  60

gac ctt gac tca ggc gtt aaa caa gtt gtt tgg aca cct cat ttt gac      240
Asp Leu Asp Ser Gly Val Lys Gln Val Val Trp Thr Pro His Phe Asp
65                  70                  75                  80

ggc tat gga ggt cgc cct gct ggt tgt caa tca gac cat gag gac aac      288
Gly Tyr Gly Gly Arg Pro Ala Gly Cys Gln Ser Asp His Glu Asp Asn
                85                  90                  95

atc tgg atc gca gac atg cgc ctt ggc ctt ctt aag tat aac gtt gag      336
Ile Trp Ile Ala Asp Met Arg Leu Gly Leu Leu Lys Tyr Asn Val Glu
            100                 105                 110

ggt aac tgt aaa caa ttc ggc aag gtt gac aca gac gga gag cct ctt      384
Gly Asn Cys Lys Gln Phe Gly Lys Val Asp Thr Asp Gly Glu Pro Leu
        115                 120                 125

aac ggt ggt aac gac ctt gta ttt gac cgc gac ggt aac ctt tgg ttt      432
Asn Gly Gly Asn Asp Leu Val Phe Asp Arg Asp Gly Asn Leu Trp Phe
    130                 135                 140

aca ggc cct gga tca cct atc gca cct tca cct gag gac cgc gag act      480
Thr Gly Pro Gly Ser Pro Ile Ala Pro Ser Pro Glu Asp Arg Glu Thr
145                 150                 155                 160

atc ttt act gag cct tca gga cgc atc tac tgc ctt cct aaa ggt ggc      528
Ile Phe Thr Glu Pro Ser Gly Arg Ile Tyr Cys Leu Pro Lys Gly Gly
                165                 170                 175

gag gtt cct atc aag gtt gac gac aac ttt atg ttc tgt aac gga atc      576
Glu Val Pro Ile Lys Val Asp Asp Asn Phe Met Phe Cys Asn Gly Ile
            180                 185                 190

gcg gta tca ggt aac atg ctt ctt gtt gct gag act gtt aag aac cag      624
Ala Val Ser Gly Asn Met Leu Leu Val Ala Glu Thr Val Lys Asn Gln
        195                 200                 205

atc atc gct tac gac atc acg gga cct ggc aaa gtt aag aat cgt cgc      672
Ile Ile Ala Tyr Asp Ile Thr Gly Pro Gly Lys Val Lys Asn Arg Arg
    210                 215                 220

ctt tgg gcg aaa gtt cct aaa cct gca ggc aat ggt ggc cct gac gga      720
Leu Trp Ala Lys Val Pro Lys Pro Ala Gly Asn Gly Gly Pro Asp Gly
225                 230                 235                 240

atg gac ttt gac gag act ggt cgc ctt ctt gtt gct aac tat ggc gct      768
Met Asp Phe Asp Glu Thr Gly Arg Leu Leu Val Ala Asn Tyr Gly Ala
                245                 250                 255

tca cac atc gag gta tat cct cct ggc ggt tca cag gag cct atc gta      816
Ser His Ile Glu Val Tyr Pro Pro Gly Gly Ser Gln Glu Pro Ile Val
            260                 265                 270

cgc ctt aag tgt cct ttc aaa aca ctt tca aac ctt cac ttt gct cgc      864
Arg Leu Lys Cys Pro Phe Lys Thr Leu Ser Asn Leu His Phe Ala Arg
        275                 280                 285

aac tca aac atc tgt tac gtt act gag cat gac aat ggt ggc gtt tgg      912
Asn Ser Asn Ile Cys Tyr Val Thr Glu His Asp Asn Gly Gly Val Trp
    290                 295                 300

aag ttc gag tgg gac tgt aaa ggt gct cct atg tat tgt gac act aaa      960
Lys Phe Glu Trp Asp Cys Lys Gly Ala Pro Met Tyr Cys Asp Thr Lys
305                 310                 315                 320

ctt taa                                                              966
Leu
```

<210> SEQ ID NO 2
<211> LENGTH: 321
<212> TYPE: PRT
<213> ORGANISM: Ciona savignyi

<400> SEQUENCE: 2

```
Met Ala Asp Ser Gly Ile Pro Val Ile Lys Glu Pro Gln Phe Thr Met
1               5                   10                  15

Ile Thr Lys Asp Ile Asn Gly Ser Glu Gly Pro Val Phe Asp Thr Lys
            20                  25                  30

Gly Arg Phe Tyr Ala Val Ala Pro Met Glu Ala Ala Asp Glu Asn Arg
        35                  40                  45

Glu Pro Gly Gln Phe Thr Asp Gly Ile Ala Gly Lys Leu Tyr Gln Val
    50                  55                  60

Asp Leu Asp Ser Gly Val Lys Gln Val Val Trp Thr Pro His Phe Asp
65                  70                  75                  80

Gly Tyr Gly Gly Arg Pro Ala Gly Cys Gln Ser Asp His Glu Asp Asn
                85                  90                  95

Ile Trp Ile Ala Asp Met Arg Leu Gly Leu Leu Lys Tyr Asn Val Glu
            100                 105                 110

Gly Asn Cys Lys Gln Phe Gly Lys Val Asp Thr Asp Gly Glu Pro Leu
        115                 120                 125

Asn Gly Gly Asn Asp Leu Val Phe Asp Arg Asp Gly Asn Leu Trp Phe
    130                 135                 140

Thr Gly Pro Gly Ser Pro Ile Ala Pro Ser Pro Glu Asp Arg Glu Thr
145                 150                 155                 160

Ile Phe Thr Glu Pro Ser Gly Arg Ile Tyr Cys Leu Pro Lys Gly Gly
                165                 170                 175

Glu Val Pro Ile Lys Val Asp Asp Asn Phe Met Phe Cys Asn Gly Ile
            180                 185                 190

Ala Val Ser Gly Asn Met Leu Leu Val Ala Glu Thr Val Lys Asn Gln
        195                 200                 205

Ile Ile Ala Tyr Asp Ile Thr Gly Pro Gly Lys Val Lys Asn Arg Arg
    210                 215                 220

Leu Trp Ala Lys Val Pro Lys Pro Ala Gly Asn Gly Gly Pro Asp Gly
225                 230                 235                 240

Met Asp Phe Asp Glu Thr Gly Arg Leu Leu Val Ala Asn Tyr Gly Ala
                245                 250                 255

Ser His Ile Glu Val Tyr Pro Pro Gly Gly Ser Gln Glu Pro Ile Val
            260                 265                 270

Arg Leu Lys Cys Pro Phe Lys Thr Leu Ser Asn Leu His Phe Ala Arg
        275                 280                 285

Asn Ser Asn Ile Cys Tyr Val Thr Glu His Asp Asn Gly Gly Val Trp
    290                 295                 300

Lys Phe Glu Trp Asp Cys Lys Gly Ala Pro Met Tyr Cys Asp Thr Lys
305                 310                 315                 320

Leu
```

<210> SEQ ID NO 3
<211> LENGTH: 945
<212> TYPE: DNA
<213> ORGANISM: Ciona intestinalis
<220> FEATURE:
<221> NAME/KEY: CDS
<222> LOCATION: (1)..(942)

<400> SEQUENCE: 3

-continued

```
atg gcg aaa aca atc gag cct aag ttc aaa atg gta act aaa gac atc       48
Met Ala Lys Thr Ile Glu Pro Lys Phe Lys Met Val Thr Lys Asp Ile
1               5                   10                  15

gac ggc tca gag ggt cct gtt ttc gac act aaa ggt cgc ttc tat gca       96
Asp Gly Ser Glu Gly Pro Val Phe Asp Thr Lys Gly Arg Phe Tyr Ala
            20                  25                  30

gta gct cct atg gag tca gct gac gac aac cgc gag act ggc caa ttc      144
Val Ala Pro Met Glu Ser Ala Asp Asp Asn Arg Glu Thr Gly Gln Phe
        35                  40                  45

ctt gac gga atc gct ggc aaa ctt tac tca gta aac ctt aac act ggt      192
Leu Asp Gly Ile Ala Gly Lys Leu Tyr Ser Val Asn Leu Asn Thr Gly
    50                  55                  60

gag aaa caa gtt gtt tgc act cct cag ttt aac ggc tat ggt ggt cgc      240
Glu Lys Gln Val Val Cys Thr Pro Gln Phe Asn Gly Tyr Gly Gly Arg
65                  70                  75                  80

cct gct ggc tgt caa tca gac aaa gag gac aac atc tgg atc gca gac      288
Pro Ala Gly Cys Gln Ser Asp Lys Glu Asp Asn Ile Trp Ile Ala Asp
                85                  90                  95

atg cgc ctt ggc ctt ctt aag tat gac ggc aaa ggc aac tgc aaa caa      336
Met Arg Leu Gly Leu Leu Lys Tyr Asp Gly Lys Gly Asn Cys Lys Gln
            100                 105                 110

ttc tca gtt gtt gac act gac gga aac cct ctt aat ggc gct aac gac      384
Phe Ser Val Val Asp Thr Asp Gly Asn Pro Leu Asn Gly Ala Asn Asp
        115                 120                 125

ctt gta ttt gac gac gac ggc aac ctt tgg ttt act gga cct ggc tca      432
Leu Val Phe Asp Asp Asp Gly Asn Leu Trp Phe Thr Gly Pro Gly Ser
    130                 135                 140

cct gtt gct cct tca gta gag gac cgc acg acg atc ttc gcg gag cct      480
Pro Val Ala Pro Ser Val Glu Asp Arg Thr Thr Ile Phe Ala Glu Pro
145                 150                 155                 160

aca ggt cgc atc tac tgc ctt cct aaa ggc tca gag gtt cct atc aaa      528
Thr Gly Arg Ile Tyr Cys Leu Pro Lys Gly Ser Glu Val Pro Ile Lys
                165                 170                 175

gtt gac gac aac ttc cgc ttt tgt aac ggc atc gct gta aca ggc aaa      576
Val Asp Asp Asn Phe Arg Phe Cys Asn Gly Ile Ala Val Thr Gly Lys
            180                 185                 190

ctt ctt ctt gta gct gag aca atg act aaa caa atc atc gca tac gac      624
Leu Leu Leu Val Ala Glu Thr Met Thr Lys Gln Ile Ile Ala Tyr Asp
        195                 200                 205

gtt act ggt cct ggc aac gta act aat cgt cgc atc tgg tct aaa gtt      672
Val Thr Gly Pro Gly Asn Val Thr Asn Arg Arg Ile Trp Ser Lys Val
    210                 215                 220

cct aaa ggc gct gag cag gga ggt cct gac gga atg gac ttc gac gaa      720
Pro Lys Gly Ala Glu Gln Gly Gly Pro Asp Gly Met Asp Phe Asp Glu
225                 230                 235                 240

cgc gga tgc ctt ctt gtt gct aac cat ggt ggt tca cac atc gag gta      768
Arg Gly Cys Leu Leu Val Ala Asn His Gly Gly Ser His Ile Glu Val
                245                 250                 255

tac cct cct gag gga ggc gac gag cct atc atc cgc gta cgc tgc cct      816
Tyr Pro Pro Glu Gly Gly Asp Glu Pro Ile Ile Arg Val Arg Cys Pro
            260                 265                 270

ttc aaa acg cct tca aac gtt cat ttc gca cag aac tca aac gta tgc      864
Phe Lys Thr Pro Ser Asn Val His Phe Ala Gln Asn Ser Asn Val Cys
        275                 280                 285

tat gtt act gag cac gac aca aac gga gtt tgg gct ttc gag tgg gac      912
Tyr Val Thr Glu His Asp Thr Asn Gly Val Trp Ala Phe Glu Trp Asp
    290                 295                 300

tgc aaa gga gca ctt atg tac tgt gac aaa taa                          945
Cys Lys Gly Ala Leu Met Tyr Cys Asp Lys
```

305 310

<210> SEQ ID NO 4
<211> LENGTH: 314
<212> TYPE: PRT
<213> ORGANISM: Ciona intestinalis

<400> SEQUENCE: 4

Met Ala Lys Thr Ile Glu Pro Lys Phe Lys Met Val Thr Lys Asp Ile
1 5 10 15

Asp Gly Ser Glu Gly Pro Val Phe Asp Thr Lys Gly Arg Phe Tyr Ala
20 25 30

Val Ala Pro Met Glu Ser Ala Asp Asp Asn Arg Glu Thr Gly Gln Phe
35 40 45

Leu Asp Gly Ile Ala Gly Lys Leu Tyr Ser Val Asn Leu Asn Thr Gly
50 55 60

Glu Lys Gln Val Val Cys Thr Pro Gln Phe Asn Gly Tyr Gly Gly Arg
65 70 75 80

Pro Ala Gly Cys Gln Ser Asp Lys Glu Asp Asn Ile Trp Ile Ala Asp
85 90 95

Met Arg Leu Gly Leu Leu Lys Tyr Asp Gly Lys Gly Asn Cys Lys Gln
100 105 110

Phe Ser Val Val Asp Thr Asp Gly Asn Pro Leu Asn Gly Ala Asn Asp
115 120 125

Leu Val Phe Asp Asp Asp Gly Asn Leu Trp Phe Thr Gly Pro Gly Ser
130 135 140

Pro Val Ala Pro Ser Val Glu Asp Arg Thr Thr Ile Phe Ala Glu Pro
145 150 155 160

Thr Gly Arg Ile Tyr Cys Leu Pro Lys Gly Ser Glu Val Pro Ile Lys
165 170 175

Val Asp Asp Asn Phe Arg Phe Cys Asn Gly Ile Ala Val Thr Gly Lys
180 185 190

Leu Leu Leu Val Ala Glu Thr Met Thr Lys Gln Ile Ile Ala Tyr Asp
195 200 205

Val Thr Gly Pro Gly Asn Val Thr Asn Arg Arg Ile Trp Ser Lys Val
210 215 220

Pro Lys Gly Ala Glu Gln Gly Gly Pro Asp Gly Met Asp Phe Asp Glu
225 230 235 240

Arg Gly Cys Leu Leu Val Ala Asn His Gly Gly Ser His Ile Glu Val
245 250 255

Tyr Pro Pro Glu Gly Gly Asp Glu Pro Ile Ile Arg Val Arg Cys Pro
260 265 270

Phe Lys Thr Pro Ser Asn Val His Phe Ala Gln Asn Ser Asn Val Cys
275 280 285

Tyr Val Thr Glu His Asp Thr Asn Gly Val Trp Ala Phe Glu Trp Asp
290 295 300

Cys Lys Gly Ala Leu Met Tyr Cys Asp Lys
305 310

<210> SEQ ID NO 5
<211> LENGTH: 1032
<212> TYPE: DNA
<213> ORGANISM: Ciona savignyi
<220> FEATURE:
<221> NAME/KEY: CDS
<222> LOCATION: (1)..(1029)

-continued

<400> SEQUENCE: 5

```
atg gca cat cac cac cac cat cac gtg ggt acc ggt tcg aat gat gac       48
Met Ala His His His His His His Val Gly Thr Gly Ser Asn Asp Asp
1               5                   10                  15

gac gac aag agt ccg gat ccc gca gac tca gga atc cct gtt atc aaa       96
Asp Asp Lys Ser Pro Asp Pro Ala Asp Ser Gly Ile Pro Val Ile Lys
            20                  25                  30

gag cct caa ttc aca atg atc act aaa gac atc aac ggc tca gaa ggc      144
Glu Pro Gln Phe Thr Met Ile Thr Lys Asp Ile Asn Gly Ser Glu Gly
        35                  40                  45

cct gtt ttc gac aca aaa ggt cgc ttc tat gcg gtt gcg cct atg gag      192
Pro Val Phe Asp Thr Lys Gly Arg Phe Tyr Ala Val Ala Pro Met Glu
    50                  55                  60

gct gcg gac gag aac cgc gag cct ggt cag ttt act gac ggc atc gca      240
Ala Ala Asp Glu Asn Arg Glu Pro Gly Gln Phe Thr Asp Gly Ile Ala
65                  70                  75                  80

gga aaa ctt tac caa gtt gac ctt gac tca ggc gtt aaa caa gtt gtt      288
Gly Lys Leu Tyr Gln Val Asp Leu Asp Ser Gly Val Lys Gln Val Val
                85                  90                  95

tgg aca cct cat ttt gac ggc tat gga ggt cgc cct gct ggt tgt caa      336
Trp Thr Pro His Phe Asp Gly Tyr Gly Gly Arg Pro Ala Gly Cys Gln
            100                 105                 110

tca gac cat gag gac aac atc tgg atc gca gac atg cgc ctt ggc ctt      384
Ser Asp His Glu Asp Asn Ile Trp Ile Ala Asp Met Arg Leu Gly Leu
        115                 120                 125

ctt aag tat aac gtt gag ggt aac tgt aaa caa ttc ggc aag gtt gac      432
Leu Lys Tyr Asn Val Glu Gly Asn Cys Lys Gln Phe Gly Lys Val Asp
    130                 135                 140

aca gac gga gag cct ctt aac ggt ggt aac gac ctt gta ttt gac cgc      480
Thr Asp Gly Glu Pro Leu Asn Gly Gly Asn Asp Leu Val Phe Asp Arg
145                 150                 155                 160

gac ggt aac ctt tgg ttt aca ggc cct gga tca cct atc gca cct tca      528
Asp Gly Asn Leu Trp Phe Thr Gly Pro Gly Ser Pro Ile Ala Pro Ser
                165                 170                 175

cct gag gac cgc gag act atc ttt act gag cct tca gga cgc atc tac      576
Pro Glu Asp Arg Glu Thr Ile Phe Thr Glu Pro Ser Gly Arg Ile Tyr
            180                 185                 190

tgc ctt cct aaa ggt ggc gag gtt cct atc aag gtt gac gac aac ttt      624
Cys Leu Pro Lys Gly Gly Glu Val Pro Ile Lys Val Asp Asp Asn Phe
        195                 200                 205

atg ttc tgt aac gga atc gcg gta tca ggt aac atg ctt ctt gtt gct      672
Met Phe Cys Asn Gly Ile Ala Val Ser Gly Asn Met Leu Leu Val Ala
    210                 215                 220

gag act gtt aag aac cag atc atc gct tac gac atc acg gga cct ggc      720
Glu Thr Val Lys Asn Gln Ile Ile Ala Tyr Asp Ile Thr Gly Pro Gly
225                 230                 235                 240

aaa gtt aag aat cgt cgc ctt tgg gcg aaa gtt cct aaa cct gca ggc      768
Lys Val Lys Asn Arg Arg Leu Trp Ala Lys Val Pro Lys Pro Ala Gly
                245                 250                 255

aat ggt ggc cct gac gga atg gac ttt gac gag act ggt cgc ctt ctt      816
Asn Gly Gly Pro Asp Gly Met Asp Phe Asp Glu Thr Gly Arg Leu Leu
            260                 265                 270

gtt gct aac tat ggc gct tca cac atc gag gta tat cct cct ggc ggt      864
Val Ala Asn Tyr Gly Ala Ser His Ile Glu Val Tyr Pro Pro Gly Gly
        275                 280                 285

tca cag gag cct atc gta cgc ctt aag tgt cct ttc aaa aca ctt tca      912
Ser Gln Glu Pro Ile Val Arg Leu Lys Cys Pro Phe Lys Thr Leu Ser
    290                 295                 300

aac ctt cac ttt gct cgc aac tca aac atc tgt tac gtt act gag cat      960
```

-continued

```
Asn Leu His Phe Ala Arg Asn Ser Asn Ile Cys Tyr Val Thr Glu His
305                 310                 315                 320

gac aat ggt ggc gtt tgg aag ttc gag tgg gac tgt aaa ggt gct cct      1008
Asp Asn Gly Gly Val Trp Lys Phe Glu Trp Asp Cys Lys Gly Ala Pro
                325                 330                 335

atg tat tgt gac act aaa ctt taa                                      1032
Met Tyr Cys Asp Thr Lys Leu
            340


<210> SEQ ID NO 6
<211> LENGTH: 343
<212> TYPE: PRT
<213> ORGANISM: Ciona savignyi

<400> SEQUENCE: 6

Met Ala His His His His His His Val Gly Thr Gly Ser Asn Asp Asp
1               5                   10                  15

Asp Asp Lys Ser Pro Asp Pro Ala Asp Ser Gly Ile Pro Val Ile Lys
            20                  25                  30

Glu Pro Gln Phe Thr Met Ile Thr Lys Asp Ile Asn Gly Ser Glu Gly
        35                  40                  45

Pro Val Phe Asp Thr Lys Gly Arg Phe Tyr Ala Val Ala Pro Met Glu
    50                  55                  60

Ala Ala Asp Glu Asn Arg Glu Pro Gly Gln Phe Thr Asp Gly Ile Ala
65                  70                  75                  80

Gly Lys Leu Tyr Gln Val Asp Leu Asp Ser Gly Val Lys Gln Val Val
                85                  90                  95

Trp Thr Pro His Phe Asp Gly Tyr Gly Gly Arg Pro Ala Gly Cys Gln
            100                 105                 110

Ser Asp His Glu Asp Asn Ile Trp Ile Ala Asp Met Arg Leu Gly Leu
        115                 120                 125

Leu Lys Tyr Asn Val Glu Gly Asn Cys Lys Gln Phe Gly Lys Val Asp
    130                 135                 140

Thr Asp Gly Glu Pro Leu Asn Gly Gly Asn Asp Leu Val Phe Asp Arg
145                 150                 155                 160

Asp Gly Asn Leu Trp Phe Thr Gly Pro Gly Ser Pro Ile Ala Pro Ser
                165                 170                 175

Pro Glu Asp Arg Glu Thr Ile Phe Thr Glu Pro Ser Gly Arg Ile Tyr
            180                 185                 190

Cys Leu Pro Lys Gly Gly Glu Val Pro Ile Lys Val Asp Asp Asn Phe
        195                 200                 205

Met Phe Cys Asn Gly Ile Ala Val Ser Gly Asn Met Leu Leu Val Ala
    210                 215                 220

Glu Thr Val Lys Asn Gln Ile Ile Ala Tyr Asp Ile Thr Gly Pro Gly
225                 230                 235                 240

Lys Val Lys Asn Arg Arg Leu Trp Ala Lys Val Pro Lys Pro Ala Gly
                245                 250                 255

Asn Gly Gly Pro Asp Gly Met Asp Phe Asp Glu Thr Gly Arg Leu Leu
            260                 265                 270

Val Ala Asn Tyr Gly Ala Ser His Ile Glu Val Tyr Pro Pro Gly Gly
        275                 280                 285

Ser Gln Glu Pro Ile Val Arg Leu Lys Cys Pro Phe Lys Thr Leu Ser
    290                 295                 300

Asn Leu His Phe Ala Arg Asn Ser Asn Ile Cys Tyr Val Thr Glu His
305                 310                 315                 320
```

```
Asp Asn Gly Gly Val Trp Lys Phe Glu Trp Asp Cys Lys Gly Ala Pro
                325                 330                 335

Met Tyr Cys Asp Thr Lys Leu
            340


<210> SEQ ID NO 7
<211> LENGTH: 1011
<212> TYPE: DNA
<213> ORGANISM: Ciona intestinalis
<220> FEATURE:
<221> NAME/KEY: CDS
<222> LOCATION: (1)..(1008)

<400> SEQUENCE: 7

atg gca cat cac cac cac cat cac gtg ggt acc ggt tcg aat gat gac       48
Met Ala His His His His His His Val Gly Thr Gly Ser Asn Asp Asp
1               5                   10                  15

gac gac aag agt ccg gat ccc gcg aaa aca atc gag cct aag ttc aaa       96
Asp Asp Lys Ser Pro Asp Pro Ala Lys Thr Ile Glu Pro Lys Phe Lys
            20                  25                  30

atg gta act aaa gac atc gac ggc tca gag ggt cct gtt ttc gac act      144
Met Val Thr Lys Asp Ile Asp Gly Ser Glu Gly Pro Val Phe Asp Thr
        35                  40                  45

aaa ggt cgc ttc tat gca gta gct cct atg gag tca gct gac gac aac      192
Lys Gly Arg Phe Tyr Ala Val Ala Pro Met Glu Ser Ala Asp Asp Asn
    50                  55                  60

cgc gag act ggc caa ttc ctt gac gga atc gct ggc aaa ctt tac tca      240
Arg Glu Thr Gly Gln Phe Leu Asp Gly Ile Ala Gly Lys Leu Tyr Ser
65                  70                  75                  80

gta aac ctt aac act ggt gag aaa caa gtt gtt tgc act cct cag ttt      288
Val Asn Leu Asn Thr Gly Glu Lys Gln Val Val Cys Thr Pro Gln Phe
                85                  90                  95

aac ggc tat ggt ggt cgc cct gct ggc tgt caa tca gac aaa gag gac      336
Asn Gly Tyr Gly Gly Arg Pro Ala Gly Cys Gln Ser Asp Lys Glu Asp
            100                 105                 110

aac atc tgg atc gca gac atg cgc ctt ggc ctt ctt aag tat gac ggc      384
Asn Ile Trp Ile Ala Asp Met Arg Leu Gly Leu Leu Lys Tyr Asp Gly
        115                 120                 125

aaa ggc aac tgc aaa caa ttc tca gtt gtt gac act gac gga aac cct      432
Lys Gly Asn Cys Lys Gln Phe Ser Val Val Asp Thr Asp Gly Asn Pro
    130                 135                 140

ctt aat ggc gct aac gac ctt gta ttt gac gac gac ggc aac ctt tgg      480
Leu Asn Gly Ala Asn Asp Leu Val Phe Asp Asp Asp Gly Asn Leu Trp
145                 150                 155                 160

ttt act gga cct ggc tca cct gtt gct cct tca gta gag gac cgc acg      528
Phe Thr Gly Pro Gly Ser Pro Val Ala Pro Ser Val Glu Asp Arg Thr
                165                 170                 175

acg atc ttc gcg gag cct aca ggt cgc atc tac tgc ctt cct aaa ggc      576
Thr Ile Phe Ala Glu Pro Thr Gly Arg Ile Tyr Cys Leu Pro Lys Gly
            180                 185                 190

tca gag gtt cct atc aaa gtt gac gac aac ttc cgc ttt tgt aac ggc      624
Ser Glu Val Pro Ile Lys Val Asp Asp Asn Phe Arg Phe Cys Asn Gly
        195                 200                 205

atc gct gta aca ggc aaa ctt ctt ctt gta gct gag aca atg act aaa      672
Ile Ala Val Thr Gly Lys Leu Leu Leu Val Ala Glu Thr Met Thr Lys
    210                 215                 220

caa atc atc gca tac gac gtt act ggt cct ggc aac gta act aat cgt      720
Gln Ile Ile Ala Tyr Asp Val Thr Gly Pro Gly Asn Val Thr Asn Arg
225                 230                 235                 240

cgc atc tgg tct aaa gtt cct aaa ggc gct gag cag gga ggt cct gac      768
Arg Ile Trp Ser Lys Val Pro Lys Gly Ala Glu Gln Gly Gly Pro Asp
```

```
                245                 250                 255

gga atg gac ttc gac gaa cgc gga tgc ctt ctt gtt gct aac cat ggt      816
Gly Met Asp Phe Asp Glu Arg Gly Cys Leu Leu Val Ala Asn His Gly
            260                 265                 270

ggt tca cac atc gag gta tac cct cct gag gga ggc gac gag cct atc      864
Gly Ser His Ile Glu Val Tyr Pro Pro Glu Gly Gly Asp Glu Pro Ile
        275                 280                 285

atc cgc gta cgc tgc cct ttc aaa acg cct tca aac gtt cat ttc gca      912
Ile Arg Val Arg Cys Pro Phe Lys Thr Pro Ser Asn Val His Phe Ala
    290                 295                 300

cag aac tca aac gta tgc tat gtt act gag cac gac aca aac gga gtt      960
Gln Asn Ser Asn Val Cys Tyr Val Thr Glu His Asp Thr Asn Gly Val
305                 310                 315                 320

tgg gct ttc gag tgg gac tgc aaa gga gca ctt atg tac tgt gac aaa     1008
Trp Ala Phe Glu Trp Asp Cys Lys Gly Ala Leu Met Tyr Cys Asp Lys
                325                 330                 335

taa                                                                 1011


<210> SEQ ID NO 8
<211> LENGTH: 336
<212> TYPE: PRT
<213> ORGANISM: Ciona intestinalis

<400> SEQUENCE: 8

Met Ala His His His His His His Val Gly Thr Gly Ser Asn Asp Asp
1               5                   10                  15

Asp Asp Lys Ser Pro Asp Pro Ala Lys Thr Ile Glu Pro Lys Phe Lys
            20                  25                  30

Met Val Thr Lys Asp Ile Asp Gly Ser Glu Gly Pro Val Phe Asp Thr
        35                  40                  45

Lys Gly Arg Phe Tyr Ala Val Ala Pro Met Glu Ser Ala Asp Asp Asn
    50                  55                  60

Arg Glu Thr Gly Gln Phe Leu Asp Gly Ile Ala Gly Lys Leu Tyr Ser
65                  70                  75                  80

Val Asn Leu Asn Thr Gly Glu Lys Gln Val Val Cys Thr Pro Gln Phe
                85                  90                  95

Asn Gly Tyr Gly Gly Arg Pro Ala Gly Cys Gln Ser Asp Lys Glu Asp
            100                 105                 110

Asn Ile Trp Ile Ala Asp Met Arg Leu Gly Leu Leu Lys Tyr Asp Gly
        115                 120                 125

Lys Gly Asn Cys Lys Gln Phe Ser Val Val Asp Thr Asp Gly Asn Pro
    130                 135                 140

Leu Asn Gly Ala Asn Asp Leu Val Phe Asp Asp Asp Gly Asn Leu Trp
145                 150                 155                 160

Phe Thr Gly Pro Gly Ser Pro Val Ala Pro Ser Val Glu Asp Arg Thr
                165                 170                 175

Thr Ile Phe Ala Glu Pro Thr Gly Arg Ile Tyr Cys Leu Pro Lys Gly
            180                 185                 190

Ser Glu Val Pro Ile Lys Val Asp Asp Asn Phe Arg Phe Cys Asn Gly
        195                 200                 205

Ile Ala Val Thr Gly Lys Leu Leu Leu Val Ala Glu Thr Met Thr Lys
    210                 215                 220

Gln Ile Ile Ala Tyr Asp Val Thr Gly Pro Gly Asn Val Thr Asn Arg
225                 230                 235                 240

Arg Ile Trp Ser Lys Val Pro Lys Gly Ala Glu Gln Gly Gly Pro Asp
                245                 250                 255
```

Gly Met Asp Phe Asp Glu Arg Gly Cys Leu Leu Val Ala Asn His Gly
260 265 270

Gly Ser His Ile Glu Val Tyr Pro Pro Glu Gly Gly Asp Glu Pro Ile
275 280 285

Ile Arg Val Arg Cys Pro Phe Lys Thr Pro Ser Asn Val His Phe Ala
290 295 300

Gln Asn Ser Asn Val Cys Tyr Val Thr Glu His Asp Thr Asn Gly Val
305 310 315 320

Trp Ala Phe Glu Trp Asp Cys Lys Gly Ala Leu Met Tyr Cys Asp Lys
325 330 335

<210> SEQ ID NO 9
<211> LENGTH: 343
<212> TYPE: PRT
<213> ORGANISM: Artificial
<220> FEATURE:
<223> OTHER INFORMATION: CSAV variant

<400> SEQUENCE: 9

Met Ala His His His His His His Val Gly Thr Gly Ser Asn Asp Asp
1 5 10 15

Asp Asp Lys Ser Pro Asp Pro Ala Asp Ser Gly Ile Pro Val Ile Lys
20 25 30

Glu Pro Gln Phe Thr Met Ile Thr Lys Asp Ile Asn Gly Ser Glu Gly
35 40 45

Pro Val Phe Asp Thr Lys Gly Arg Phe Tyr Ala Val Ala Pro Ala Glu
50 55 60

Ala Ala Asp Glu Asn Arg Glu Pro Gly Gln Phe Thr Asp Gly Ile Ala
65 70 75 80

Gly Lys Leu Tyr Gln Val Asp Leu Asp Ser Gly Val Lys Gln Val Val
85 90 95

Trp Thr Pro His Phe Asp Gly Tyr Gly Gly Arg Pro Ala Gly Cys Gln
100 105 110

Ser Asp His Glu Asp Asn Ile Trp Ile Ala Asp Met Arg Leu Gly Leu
115 120 125

Leu Lys Tyr Asn Val Glu Gly Asn Cys Lys Gln Phe Gly Lys Val Asp
130 135 140

Thr Asp Gly Glu Pro Leu Asn Gly Gly Asn Asp Leu Val Phe Asp Arg
145 150 155 160

Asp Gly Asn Leu Trp Phe Thr Gly Pro Gly Ser Pro Ile Ala Pro Ser
165 170 175

Pro Glu Asp Arg Glu Thr Ile Phe Thr Glu Pro Ser Gly Arg Ile Tyr
180 185 190

Cys Leu Pro Lys Gly Gly Glu Val Pro Ile Lys Val Asp Asp Asn Phe
195 200 205

Met Phe Cys Asn Gly Ile Ala Val Ser Gly Asn Met Leu Leu Val Ala
210 215 220

Glu Thr Val Lys Asn Gln Ile Ile Ala Tyr Asp Ile Thr Gly Pro Gly
225 230 235 240

Lys Val Lys Asn Arg Arg Leu Trp Ala Lys Val Pro Lys Pro Ala Gly
245 250 255

Asn Gly Gly Pro Asp Gly Met Asp Phe Asp Glu Thr Gly Arg Leu Leu
260 265 270

Val Ala Asn Tyr Gly Ala Ser His Ile Glu Val Tyr Pro Pro Gly Gly
275 280 285

Ser Gln Glu Pro Ile Val Arg Leu Lys Cys Pro Phe Lys Thr Leu Ser
    290                 295                 300

Asn Leu His Phe Ala Arg Asn Ser Asn Ile Cys Tyr Val Thr Glu His
305                 310                 315                 320

Asp Asn Gly Gly Val Trp Lys Phe Glu Trp Asp Cys Lys Gly Ala Pro
                325                 330                 335

Met Tyr Cys Asp Thr Lys Leu
            340

<210> SEQ ID NO 10
<211> LENGTH: 343
<212> TYPE: PRT
<213> ORGANISM: Artificial
<220> FEATURE:
<223> OTHER INFORMATION: CSAV variant

<400> SEQUENCE: 10

Met Ala His His His His His His Val Gly Thr Gly Ser Asn Asp Asp
1               5                   10                  15

Asp Asp Lys Ser Pro Asp Pro Ala Asp Ser Gly Ile Pro Val Ile Lys
            20                  25                  30

Glu Pro Gln Phe Thr Met Ile Thr Lys Asp Ile Asn Gly Ser Glu Gly
        35                  40                  45

Pro Val Phe Asp Thr Lys Gly Arg Phe Tyr Ala Val Ala Pro Gly Glu
    50                  55                  60

Ala Ala Asp Glu Asn Arg Glu Pro Gly Gln Phe Thr Asp Gly Ile Ala
65                  70                  75                  80

Gly Lys Leu Tyr Gln Val Asp Leu Asp Ser Gly Val Lys Gln Val Val
                85                  90                  95

Trp Thr Pro His Phe Asp Gly Tyr Gly Gly Arg Pro Ala Gly Cys Gln
            100                 105                 110

Ser Asp His Glu Asp Asn Ile Trp Ile Ala Asp Met Arg Leu Gly Leu
        115                 120                 125

Leu Lys Tyr Asn Val Glu Gly Asn Cys Lys Gln Phe Gly Lys Val Asp
    130                 135                 140

Thr Asp Gly Glu Pro Leu Asn Gly Gly Asn Asp Leu Val Phe Asp Arg
145                 150                 155                 160

Asp Gly Asn Leu Trp Phe Thr Gly Pro Gly Ser Pro Ile Ala Pro Ser
                165                 170                 175

Pro Glu Asp Arg Glu Thr Ile Phe Thr Glu Pro Ser Gly Arg Ile Tyr
            180                 185                 190

Cys Leu Pro Lys Gly Gly Glu Val Pro Ile Lys Val Asp Asp Asn Phe
        195                 200                 205

Met Phe Cys Asn Gly Ile Ala Val Ser Gly Asn Met Leu Leu Val Ala
    210                 215                 220

Glu Thr Val Lys Asn Gln Ile Ile Ala Tyr Asp Ile Thr Gly Pro Gly
225                 230                 235                 240

Lys Val Lys Asn Arg Arg Leu Trp Ala Lys Val Pro Lys Pro Ala Gly
                245                 250                 255

Asn Gly Gly Pro Asp Gly Met Asp Phe Asp Glu Thr Gly Arg Leu Leu
            260                 265                 270

Val Ala Asn Tyr Gly Ala Ser His Ile Glu Val Tyr Pro Pro Gly Gly
        275                 280                 285

Ser Gln Glu Pro Ile Val Arg Leu Lys Cys Pro Phe Lys Thr Leu Ser
    290                 295                 300

```
Asn Leu His Phe Ala Arg Asn Ser Asn Ile Cys Tyr Val Thr Glu His
305                 310                 315                 320

Asp Asn Gly Gly Val Trp Lys Phe Glu Trp Asp Cys Lys Gly Ala Pro
                325                 330                 335

Met Tyr Cys Asp Thr Lys Leu
            340


<210> SEQ ID NO 11
<211> LENGTH: 343
<212> TYPE: PRT
<213> ORGANISM: Artificial
<220> FEATURE:
<223> OTHER INFORMATION: CSAV variant

<400> SEQUENCE: 11

Met Ala His His His His His His Val Gly Thr Gly Ser Asn Asp Asp
1               5                   10                  15

Asp Asp Lys Ser Pro Asp Pro Ala Asp Ser Gly Ile Pro Val Ile Lys
            20                  25                  30

Glu Pro Gln Phe Thr Met Ile Thr Lys Asp Ile Asn Gly Ser Glu Gly
        35                  40                  45

Pro Val Phe Asp Thr Lys Gly Arg Phe Tyr Ala Val Ala Pro Met Glu
    50                  55                  60

Ala Ala Asp Glu Asn Arg Glu Pro Gly Gln Phe Thr Asp Gly Ile Ala
65                  70                  75                  80

Gly Lys Leu Tyr Gln Val Asp Leu Asp Ser Gly Val Lys Gln Val Val
                85                  90                  95

Trp Thr Pro His Phe Asp Gly Tyr Gly Gly Ile Pro Ala Gly Cys Gln
            100                 105                 110

Ser Asp His Glu Asp Asn Ile Trp Ile Ala Asp Met Arg Leu Gly Leu
        115                 120                 125

Leu Lys Tyr Asn Val Glu Gly Asn Cys Lys Gln Phe Gly Lys Val Asp
    130                 135                 140

Thr Asp Gly Glu Pro Leu Asn Gly Gly Asn Asp Leu Val Phe Asp Arg
145                 150                 155                 160

Asp Gly Asn Leu Trp Phe Thr Gly Pro Gly Ser Pro Ile Ala Pro Ser
                165                 170                 175

Pro Glu Asp Arg Glu Thr Ile Phe Thr Glu Pro Ser Gly Arg Ile Tyr
            180                 185                 190

Cys Leu Pro Lys Gly Gly Glu Val Pro Ile Lys Val Asp Asp Asn Phe
        195                 200                 205

Met Phe Cys Asn Gly Ile Ala Val Ser Gly Asn Met Leu Leu Val Ala
    210                 215                 220

Glu Thr Val Lys Asn Gln Ile Ile Ala Tyr Asp Ile Thr Gly Pro Gly
225                 230                 235                 240

Lys Val Lys Asn Arg Arg Leu Trp Ala Lys Val Pro Lys Pro Ala Gly
                245                 250                 255

Asn Gly Gly Pro Asp Gly Met Asp Phe Asp Glu Thr Gly Arg Leu Leu
            260                 265                 270

Val Ala Asn Tyr Gly Ala Ser His Ile Glu Val Tyr Pro Pro Gly Gly
        275                 280                 285

Ser Gln Glu Pro Ile Val Arg Leu Lys Cys Pro Phe Lys Thr Leu Ser
    290                 295                 300

Asn Leu His Phe Ala Arg Asn Ser Asn Ile Cys Tyr Val Thr Glu His
305                 310                 315                 320
```

```
Asp Asn Gly Gly Val Trp Lys Phe Glu Trp Asp Cys Lys Gly Ala Pro
                325                 330                 335

Met Tyr Cys Asp Thr Lys Leu
            340


<210> SEQ ID NO 12
<211> LENGTH: 343
<212> TYPE: PRT
<213> ORGANISM: Artificial
<220> FEATURE:
<223> OTHER INFORMATION: CSAV variant

<400> SEQUENCE: 12

Met Ala His His His His His His Val Gly Thr Gly Ser Asn Asp Asp
1               5                   10                  15

Asp Asp Lys Ser Pro Asp Pro Ala Asp Ser Gly Ile Pro Val Ile Lys
            20                  25                  30

Glu Pro Gln Phe Thr Met Ile Thr Lys Asp Ile Asn Gly Ser Glu Gly
        35                  40                  45

Pro Val Phe Asp Thr Lys Gly Arg Phe Tyr Ala Val Ala Pro Met Glu
    50                  55                  60

Ala Ala Asp Glu Asn Arg Glu Pro Gly Gln Phe Thr Asp Gly Ile Ala
65                  70                  75                  80

Gly Lys Leu Tyr Gln Val Asp Leu Asp Ser Gly Val Lys Gln Val Val
                85                  90                  95

Trp Thr Pro His Phe Asp Gly Tyr Gly Gly Val Pro Ala Gly Cys Gln
            100                 105                 110

Ser Asp His Glu Asp Asn Ile Trp Ile Ala Asp Met Arg Leu Gly Leu
        115                 120                 125

Leu Lys Tyr Asn Val Glu Gly Asn Cys Lys Gln Phe Gly Lys Val Asp
    130                 135                 140

Thr Asp Gly Glu Pro Leu Asn Gly Gly Asn Asp Leu Val Phe Asp Arg
145                 150                 155                 160

Asp Gly Asn Leu Trp Phe Thr Gly Pro Gly Ser Pro Ile Ala Pro Ser
                165                 170                 175

Pro Glu Asp Arg Glu Thr Ile Phe Thr Glu Pro Ser Gly Arg Ile Tyr
            180                 185                 190

Cys Leu Pro Lys Gly Gly Glu Val Pro Ile Lys Val Asp Asp Asn Phe
        195                 200                 205

Met Phe Cys Asn Gly Ile Ala Val Ser Gly Asn Met Leu Leu Val Ala
    210                 215                 220

Glu Thr Val Lys Asn Gln Ile Ile Ala Tyr Asp Ile Thr Gly Pro Gly
225                 230                 235                 240

Lys Val Lys Asn Arg Arg Leu Trp Ala Lys Val Pro Lys Pro Ala Gly
                245                 250                 255

Asn Gly Gly Pro Asp Gly Met Asp Phe Asp Glu Thr Gly Arg Leu Leu
            260                 265                 270

Val Ala Asn Tyr Gly Ala Ser His Ile Glu Val Tyr Pro Pro Gly Gly
        275                 280                 285

Ser Gln Glu Pro Ile Val Arg Leu Lys Cys Pro Phe Lys Thr Leu Ser
    290                 295                 300

Asn Leu His Phe Ala Arg Asn Ser Asn Ile Cys Tyr Val Thr Glu His
305                 310                 315                 320

Asp Asn Gly Gly Val Trp Lys Phe Glu Trp Asp Cys Lys Gly Ala Pro
                325                 330                 335
```

```
Met Tyr Cys Asp Thr Lys Leu
            340


<210> SEQ ID NO 13
<211> LENGTH: 343
<212> TYPE: PRT
<213> ORGANISM: Artificial
<220> FEATURE:
<223> OTHER INFORMATION: CSAV variant

<400> SEQUENCE: 13

Met Ala His His His His His His Val Gly Thr Gly Ser Asn Asp Asp
1               5                   10                  15

Asp Asp Lys Ser Pro Asp Pro Ala Asp Ser Gly Ile Pro Val Ile Lys
            20                  25                  30

Glu Pro Gln Phe Thr Met Ile Thr Lys Asp Ile Asn Gly Ser Glu Gly
        35                  40                  45

Pro Val Phe Asp Thr Lys Gly Arg Phe Tyr Ala Val Ala Pro Met Glu
    50                  55                  60

Ala Ala Asp Glu Asn Arg Glu Pro Gly Gln Phe Thr Asp Gly Ile Ala
65                  70                  75                  80

Gly Lys Leu Tyr Gln Val Asp Leu Asp Ser Gly Val Lys Gln Val Val
                85                  90                  95

Trp Thr Pro His Phe Asp Gly Tyr Gly Gly Leu Pro Ala Gly Cys Gln
            100                 105                 110

Ser Asp His Glu Asp Asn Ile Trp Ile Ala Asp Met Arg Leu Gly Leu
        115                 120                 125

Leu Lys Tyr Asn Val Glu Gly Asn Cys Lys Gln Phe Gly Lys Val Asp
    130                 135                 140

Thr Asp Gly Glu Pro Leu Asn Gly Gly Asn Asp Leu Val Phe Asp Arg
145                 150                 155                 160

Asp Gly Asn Leu Trp Phe Thr Gly Pro Gly Ser Pro Ile Ala Pro Ser
                165                 170                 175

Pro Glu Asp Arg Glu Thr Ile Phe Thr Glu Pro Ser Gly Arg Ile Tyr
            180                 185                 190

Cys Leu Pro Lys Gly Gly Glu Val Pro Ile Lys Val Asp Asp Asn Phe
        195                 200                 205

Met Phe Cys Asn Gly Ile Ala Val Ser Gly Asn Met Leu Leu Val Ala
    210                 215                 220

Glu Thr Val Lys Asn Gln Ile Ile Ala Tyr Asp Ile Thr Gly Pro Gly
225                 230                 235                 240

Lys Val Lys Asn Arg Arg Leu Trp Ala Lys Val Pro Lys Pro Ala Gly
                245                 250                 255

Asn Gly Gly Pro Asp Gly Met Asp Phe Asp Glu Thr Gly Arg Leu Leu
            260                 265                 270

Val Ala Asn Tyr Gly Ala Ser His Ile Glu Val Tyr Pro Pro Gly Gly
        275                 280                 285

Ser Gln Glu Pro Ile Val Arg Leu Lys Cys Pro Phe Lys Thr Leu Ser
    290                 295                 300

Asn Leu His Phe Ala Arg Asn Ser Asn Ile Cys Tyr Val Thr Glu His
305                 310                 315                 320

Asp Asn Gly Gly Val Trp Lys Phe Glu Trp Asp Cys Lys Gly Ala Pro
                325                 330                 335

Met Tyr Cys Asp Thr Lys Leu
            340
```

<210> SEQ ID NO 14
<211> LENGTH: 343
<212> TYPE: PRT
<213> ORGANISM: Artificial
<220> FEATURE:
<223> OTHER INFORMATION: CSAV variant

<400> SEQUENCE: 14

```
Met Ala His His His His His His Val Gly Thr Gly Ser Asn Asp Asp
1               5                   10                  15

Asp Asp Lys Ser Pro Asp Pro Ala Asp Ser Gly Ile Pro Val Ile Lys
            20                  25                  30

Glu Pro Gln Phe Thr Met Ile Thr Lys Asp Ile Asn Gly Ser Glu Gly
        35                  40                  45

Pro Val Phe Asp Thr Lys Gly Arg Phe Tyr Ala Val Ala Pro Met Glu
    50                  55                  60

Ala Ala Asp Glu Asn Arg Glu Pro Gly Gln Phe Thr Asp Gly Ile Ala
65                  70                  75                  80

Gly Lys Leu Tyr Gln Val Asp Leu Asp Ser Gly Val Lys Gln Val Val
                85                  90                  95

Trp Thr Pro His Phe Asp Gly Tyr Gly Gly Arg Pro Ser Gly Cys Gln
            100                 105                 110

Ser Asp His Glu Asp Asn Ile Trp Ile Ala Asp Met Arg Leu Gly Leu
        115                 120                 125

Leu Lys Tyr Asn Val Glu Gly Asn Cys Lys Gln Phe Gly Lys Val Asp
    130                 135                 140

Thr Asp Gly Glu Pro Leu Asn Gly Gly Asn Asp Leu Val Phe Asp Arg
145                 150                 155                 160

Asp Gly Asn Leu Trp Phe Thr Gly Pro Gly Ser Pro Ile Ala Pro Ser
                165                 170                 175

Pro Glu Asp Arg Glu Thr Ile Phe Thr Glu Pro Ser Gly Arg Ile Tyr
            180                 185                 190

Cys Leu Pro Lys Gly Gly Glu Val Pro Ile Lys Val Asp Asp Asn Phe
        195                 200                 205

Met Phe Cys Asn Gly Ile Ala Val Ser Gly Asn Met Leu Leu Val Ala
    210                 215                 220

Glu Thr Val Lys Asn Gln Ile Ile Ala Tyr Asp Ile Thr Gly Pro Gly
225                 230                 235                 240

Lys Val Lys Asn Arg Arg Leu Trp Ala Lys Val Pro Lys Pro Ala Gly
                245                 250                 255

Asn Gly Gly Pro Asp Gly Met Asp Phe Asp Glu Thr Gly Arg Leu Leu
            260                 265                 270

Val Ala Asn Tyr Gly Ala Ser His Ile Glu Val Tyr Pro Pro Gly Gly
        275                 280                 285

Ser Gln Glu Pro Ile Val Arg Leu Lys Cys Pro Phe Lys Thr Leu Ser
    290                 295                 300

Asn Leu His Phe Ala Arg Asn Ser Asn Ile Cys Tyr Val Thr Glu His
305                 310                 315                 320

Asp Asn Gly Gly Val Trp Lys Phe Glu Trp Asp Cys Lys Gly Ala Pro
                325                 330                 335

Met Tyr Cys Asp Thr Lys Leu
            340
```

<210> SEQ ID NO 15

<211> LENGTH: 343
<212> TYPE: PRT
<213> ORGANISM: Artificial
<220> FEATURE:
<223> OTHER INFORMATION: CSAV variant

<400> SEQUENCE: 15

Met Ala His His His His His His Val Gly Thr Gly Ser Asn Asp Asp
1 5 10 15

Asp Asp Lys Ser Pro Asp Pro Ala Asp Ser Gly Ile Pro Val Ile Lys
20 25 30

Glu Pro Gln Phe Thr Met Ile Thr Lys Asp Ile Asn Gly Ser Glu Gly
35 40 45

Pro Val Phe Asp Thr Lys Gly Arg Phe Tyr Ala Val Ala Pro Met Glu
50 55 60

Ala Ala Asp Glu Asn Arg Glu Pro Gly Gln Phe Thr Asp Gly Ile Ala
65 70 75 80

Gly Lys Leu Tyr Gln Val Asp Leu Asp Ser Gly Val Lys Gln Val Val
85 90 95

Trp Thr Pro His Phe Asp Gly Tyr Gly Gly Arg Pro Cys Gly Cys Gln
100 105 110

Ser Asp His Glu Asp Asn Ile Trp Ile Ala Asp Met Arg Leu Gly Leu
115 120 125

Leu Lys Tyr Asn Val Glu Gly Asn Cys Lys Gln Phe Gly Lys Val Asp
130 135 140

Thr Asp Gly Glu Pro Leu Asn Gly Gly Asn Asp Leu Val Phe Asp Arg
145 150 155 160

Asp Gly Asn Leu Trp Phe Thr Gly Pro Gly Ser Pro Ile Ala Pro Ser
165 170 175

Pro Glu Asp Arg Glu Thr Ile Phe Thr Glu Pro Ser Gly Arg Ile Tyr
180 185 190

Cys Leu Pro Lys Gly Gly Glu Val Pro Ile Lys Val Asp Asp Asn Phe
195 200 205

Met Phe Cys Asn Gly Ile Ala Val Ser Gly Asn Met Leu Leu Val Ala
210 215 220

Glu Thr Val Lys Asn Gln Ile Ile Ala Tyr Asp Ile Thr Gly Pro Gly
225 230 235 240

Lys Val Lys Asn Arg Arg Leu Trp Ala Lys Val Pro Lys Pro Ala Gly
245 250 255

Asn Gly Gly Pro Asp Gly Met Asp Phe Asp Glu Thr Gly Arg Leu Leu
260 265 270

Val Ala Asn Tyr Gly Ala Ser His Ile Glu Val Tyr Pro Pro Gly Gly
275 280 285

Ser Gln Glu Pro Ile Val Arg Leu Lys Cys Pro Phe Lys Thr Leu Ser
290 295 300

Asn Leu His Phe Ala Arg Asn Ser Asn Ile Cys Tyr Val Thr Glu His
305 310 315 320

Asp Asn Gly Gly Val Trp Lys Phe Glu Trp Asp Cys Lys Gly Ala Pro
325 330 335

Met Tyr Cys Asp Thr Lys Leu
340

<210> SEQ ID NO 16
<211> LENGTH: 343
<212> TYPE: PRT
<213> ORGANISM: Artificial

<220> FEATURE:
<223> OTHER INFORMATION: CSAV variant

<400> SEQUENCE: 16

```
Met Ala His His His His His His Val Gly Thr Gly Ser Asn Asp Asp
1               5                   10                  15

Asp Asp Lys Ser Pro Asp Pro Ala Asp Ser Gly Ile Pro Val Ile Lys
            20                  25                  30

Glu Pro Gln Phe Thr Met Ile Thr Lys Asp Ile Asn Gly Ser Glu Gly
        35                  40                  45

Pro Val Phe Asp Thr Lys Gly Arg Phe Tyr Ala Val Ala Pro Met Glu
    50                  55                  60

Ala Ala Asp Glu Asn Arg Glu Pro Gly Gln Phe Thr Asp Gly Ile Ala
65                  70                  75                  80

Gly Lys Leu Tyr Gln Val Asp Leu Asp Ser Gly Val Lys Gln Val Val
                85                  90                  95

Trp Thr Pro His Phe Asp Gly Tyr Gly Gly Arg Pro Ala Gly Cys Gln
            100                 105                 110

Ser Asp His Glu Asp Asn Ile Trp Ile Ala Asp Met Arg Leu Gly Leu
        115                 120                 125

Leu Lys Tyr Asn Val Glu Gly Asn Cys Lys Gln Phe Gly Lys Val Asp
    130                 135                 140

Thr Asp Gly Glu Pro Leu Asn Gly Gly Asn Asp Leu Val Phe Asp Arg
145                 150                 155                 160

Asp Gly Asn Leu Trp Phe Thr Gly Pro Gly Ser Pro Ile Ala Pro Ser
                165                 170                 175

Pro Phe Asp Arg Glu Thr Ile Phe Thr Glu Pro Ser Gly Arg Ile Tyr
            180                 185                 190

Cys Leu Pro Lys Gly Gly Glu Val Pro Ile Lys Val Asp Asp Asn Phe
        195                 200                 205

Met Phe Cys Asn Gly Ile Ala Val Ser Gly Asn Met Leu Leu Val Ala
    210                 215                 220

Glu Thr Val Lys Asn Gln Ile Ile Ala Tyr Asp Ile Thr Gly Pro Gly
225                 230                 235                 240

Lys Val Lys Asn Arg Arg Leu Trp Ala Lys Val Pro Lys Pro Ala Gly
                245                 250                 255

Asn Gly Gly Pro Asp Gly Met Asp Phe Asp Glu Thr Gly Arg Leu Leu
            260                 265                 270

Val Ala Asn Tyr Gly Ala Ser His Ile Glu Val Tyr Pro Pro Gly Gly
        275                 280                 285

Ser Gln Glu Pro Ile Val Arg Leu Lys Cys Pro Phe Lys Thr Leu Ser
    290                 295                 300

Asn Leu His Phe Ala Arg Asn Ser Asn Ile Cys Tyr Val Thr Glu His
305                 310                 315                 320

Asp Asn Gly Gly Val Trp Lys Phe Glu Trp Asp Cys Lys Gly Ala Pro
                325                 330                 335

Met Tyr Cys Asp Thr Lys Leu
            340
```

<210> SEQ ID NO 17
<211> LENGTH: 343
<212> TYPE: PRT
<213> ORGANISM: Artificial
<220> FEATURE:
<223> OTHER INFORMATION: CSAV variant

<400> SEQUENCE: 17

Met Ala His His His His His His Val Gly Thr Gly Ser Asn Asp Asp
1 5 10 15

Asp Asp Lys Ser Pro Asp Pro Ala Asp Ser Gly Ile Pro Val Ile Lys
20 25 30

Glu Pro Gln Phe Thr Met Ile Thr Lys Asp Ile Asn Gly Ser Glu Gly
35 40 45

Pro Val Phe Asp Thr Lys Gly Arg Phe Tyr Ala Val Ala Pro Met Glu
50 55 60

Ala Ala Asp Glu Asn Arg Glu Pro Gly Gln Phe Thr Asp Gly Ile Ala
65 70 75 80

Gly Lys Leu Tyr Gln Val Asp Leu Asp Ser Gly Val Lys Gln Val Val
85 90 95

Trp Thr Pro His Phe Asp Gly Tyr Gly Gly Arg Pro Ala Gly Cys Gln
100 105 110

Ser Asp His Glu Asp Asn Ile Trp Ile Ala Asp Met Arg Leu Gly Leu
115 120 125

Leu Lys Tyr Asn Val Glu Gly Asn Cys Lys Gln Phe Gly Lys Val Asp
130 135 140

Thr Asp Gly Glu Pro Leu Asn Gly Gly Asn Asp Leu Val Phe Asp Arg
145 150 155 160

Asp Gly Asn Leu Trp Phe Thr Gly Pro Gly Ser Pro Ile Ala Pro Ser
165 170 175

Pro Ile Asp Arg Glu Thr Ile Phe Thr Glu Pro Ser Gly Arg Ile Tyr
180 185 190

Cys Leu Pro Lys Gly Gly Glu Val Pro Ile Lys Val Asp Asp Asn Phe
195 200 205

Met Phe Cys Asn Gly Ile Ala Val Ser Gly Asn Met Leu Leu Val Ala
210 215 220

Glu Thr Val Lys Asn Gln Ile Ile Ala Tyr Asp Ile Thr Gly Pro Gly
225 230 235 240

Lys Val Lys Asn Arg Arg Leu Trp Ala Lys Val Pro Lys Pro Ala Gly
245 250 255

Asn Gly Gly Pro Asp Gly Met Asp Phe Asp Glu Thr Gly Arg Leu Leu
260 265 270

Val Ala Asn Tyr Gly Ala Ser His Ile Glu Val Tyr Pro Pro Gly Gly
275 280 285

Ser Gln Glu Pro Ile Val Arg Leu Lys Cys Pro Phe Lys Thr Leu Ser
290 295 300

Asn Leu His Phe Ala Arg Asn Ser Asn Ile Cys Tyr Val Thr Glu His
305 310 315 320

Asp Asn Gly Gly Val Trp Lys Phe Glu Trp Asp Cys Lys Gly Ala Pro
325 330 335

Met Tyr Cys Asp Thr Lys Leu
340

<210> SEQ ID NO 18
<211> LENGTH: 343
<212> TYPE: PRT
<213> ORGANISM: Artificial
<220> FEATURE:
<223> OTHER INFORMATION: CSAV variant

<400> SEQUENCE: 18

Met Ala His His His His His His Val Gly Thr Gly Ser Asn Asp Asp

-continued

```
1               5                   10                  15

Asp Asp Lys Ser Pro Asp Pro Ala Asp Ser Gly Ile Pro Val Ile Lys
            20                  25                  30

Glu Pro Gln Phe Thr Met Ile Thr Lys Asp Ile Asn Gly Ser Glu Gly
        35                  40                  45

Pro Val Phe Asp Thr Lys Gly Arg Phe Tyr Ala Val Ala Pro Met Glu
    50                  55                  60

Ala Ala Asp Glu Asn Arg Glu Pro Gly Gln Phe Thr Asp Gly Ile Ala
65                  70                  75                  80

Gly Lys Leu Tyr Gln Val Asp Leu Asp Ser Gly Val Lys Gln Val Val
                85                  90                  95

Trp Thr Pro His Phe Asp Gly Tyr Gly Gly Arg Pro Ala Gly Cys Gln
            100                 105                 110

Ser Asp His Glu Asp Asn Ile Trp Ile Ala Asp Met Arg Leu Gly Leu
        115                 120                 125

Leu Lys Tyr Asn Val Glu Gly Asn Cys Lys Gln Phe Gly Lys Val Asp
    130                 135                 140

Thr Asp Gly Glu Pro Leu Asn Gly Gly Asn Asp Leu Val Phe Asp Arg
145                 150                 155                 160

Asp Gly Asn Leu Trp Phe Thr Gly Pro Gly Ser Pro Ile Ala Pro Ser
                165                 170                 175

Pro Leu Asp Arg Glu Thr Ile Phe Thr Glu Pro Ser Gly Arg Ile Tyr
            180                 185                 190

Cys Leu Pro Lys Gly Gly Glu Val Pro Ile Lys Val Asp Asp Asn Phe
        195                 200                 205

Met Phe Cys Asn Gly Ile Ala Val Ser Gly Asn Met Leu Leu Val Ala
    210                 215                 220

Glu Thr Val Lys Asn Gln Ile Ile Ala Tyr Asp Ile Thr Gly Pro Gly
225                 230                 235                 240

Lys Val Lys Asn Arg Arg Leu Trp Ala Lys Val Pro Lys Pro Ala Gly
                245                 250                 255

Asn Gly Gly Pro Asp Gly Met Asp Phe Asp Glu Thr Gly Arg Leu Leu
            260                 265                 270

Val Ala Asn Tyr Gly Ala Ser His Ile Glu Val Tyr Pro Pro Gly Gly
        275                 280                 285

Ser Gln Glu Pro Ile Val Arg Leu Lys Cys Pro Phe Lys Thr Leu Ser
    290                 295                 300

Asn Leu His Phe Ala Arg Asn Ser Asn Ile Cys Tyr Val Thr Glu His
305                 310                 315                 320

Asp Asn Gly Gly Val Trp Lys Phe Glu Trp Asp Cys Lys Gly Ala Pro
                325                 330                 335

Met Tyr Cys Asp Thr Lys Leu
            340


<210> SEQ ID NO 19
<211> LENGTH: 343
<212> TYPE: PRT
<213> ORGANISM: Artificial
<220> FEATURE:
<223> OTHER INFORMATION: CSAV variant

<400> SEQUENCE: 19

Met Ala His His His His His His Val Gly Thr Gly Ser Asn Asp Asp
1               5                   10                  15

Asp Asp Lys Ser Pro Asp Pro Ala Asp Ser Gly Ile Pro Val Ile Lys
```

```
            20                  25                  30

Glu Pro Gln Phe Thr Met Ile Thr Lys Asp Ile Asn Gly Ser Glu Gly
        35                  40                  45

Pro Val Phe Asp Thr Lys Gly Arg Phe Tyr Ala Val Ala Pro Met Glu
    50                  55                  60

Ala Ala Asp Glu Asn Arg Glu Pro Gly Gln Phe Thr Asp Gly Ile Ala
65                  70                  75                  80

Gly Lys Leu Tyr Gln Val Asp Leu Asp Ser Gly Val Lys Gln Val Val
                85                  90                  95

Trp Thr Pro His Phe Asp Gly Tyr Gly Gly Arg Pro Ala Gly Cys Gln
            100                 105                 110

Ser Asp His Glu Asp Asn Ile Trp Ile Ala Asp Met Arg Leu Gly Leu
        115                 120                 125

Leu Lys Tyr Asn Val Glu Gly Asn Cys Lys Gln Phe Gly Lys Val Asp
    130                 135                 140

Thr Asp Gly Glu Pro Leu Asn Gly Gly Asn Asp Leu Val Phe Asp Arg
145                 150                 155                 160

Asp Gly Asn Leu Trp Phe Thr Gly Pro Gly Ser Pro Ile Ala Pro Ser
                165                 170                 175

Pro Val Asp Arg Glu Thr Ile Phe Thr Glu Pro Ser Gly Arg Ile Tyr
            180                 185                 190

Cys Leu Pro Lys Gly Gly Glu Val Pro Ile Lys Val Asp Asp Asn Phe
        195                 200                 205

Met Phe Cys Asn Gly Ile Ala Val Ser Gly Asn Met Leu Leu Val Ala
    210                 215                 220

Glu Thr Val Lys Asn Gln Ile Ile Ala Tyr Asp Ile Thr Gly Pro Gly
225                 230                 235                 240

Lys Val Lys Asn Arg Arg Leu Trp Ala Lys Val Pro Lys Pro Ala Gly
                245                 250                 255

Asn Gly Gly Pro Asp Gly Met Asp Phe Asp Glu Thr Gly Arg Leu Leu
            260                 265                 270

Val Ala Asn Tyr Gly Ala Ser His Ile Glu Val Tyr Pro Pro Gly Gly
        275                 280                 285

Ser Gln Glu Pro Ile Val Arg Leu Lys Cys Pro Phe Lys Thr Leu Ser
    290                 295                 300

Asn Leu His Phe Ala Arg Asn Ser Asn Ile Cys Tyr Val Thr Glu His
305                 310                 315                 320

Asp Asn Gly Gly Val Trp Lys Phe Glu Trp Asp Cys Lys Gly Ala Pro
                325                 330                 335

Met Tyr Cys Asp Thr Lys Leu
            340


<210> SEQ ID NO 20
<211> LENGTH: 343
<212> TYPE: PRT
<213> ORGANISM: Artificial
<220> FEATURE:
<223> OTHER INFORMATION: CSAV variant

<400> SEQUENCE: 20

Met Ala His His His His His His Val Gly Thr Gly Ser Asn Asp Asp
1               5                   10                  15

Asp Asp Lys Ser Pro Asp Pro Ala Asp Ser Gly Ile Pro Val Ile Lys
            20                  25                  30

Glu Pro Gln Phe Thr Met Ile Thr Lys Asp Ile Asn Gly Ser Glu Gly
```

35 40 45

Pro Val Phe Asp Thr Lys Gly Arg Phe Tyr Ala Val Ala Pro Met Glu
50 55 60

Ala Ala Asp Glu Asn Arg Glu Pro Gly Gln Phe Thr Asp Gly Ile Ala
65 70 75 80

Gly Lys Leu Tyr Gln Val Asp Leu Asp Ser Gly Val Lys Gln Val Val
85 90 95

Trp Thr Pro His Phe Asp Gly Tyr Gly Gly Arg Pro Ala Gly Cys Gln
100 105 110

Ser Asp His Glu Asp Asn Ile Trp Ile Ala Asp Met Arg Leu Gly Leu
115 120 125

Leu Lys Tyr Asn Val Glu Gly Asn Cys Lys Gln Phe Gly Lys Val Asp
130 135 140

Thr Asp Gly Glu Pro Leu Asn Gly Gly Asn Asp Leu Val Phe Asp Arg
145 150 155 160

Asp Gly Asn Leu Trp Phe Thr Gly Pro Gly Ser Pro Ile Ala Pro Ser
165 170 175

Pro Glu Asp Phe Glu Thr Ile Phe Thr Glu Pro Ser Gly Arg Ile Tyr
180 185 190

Cys Leu Pro Lys Gly Gly Glu Val Pro Ile Lys Val Asp Asp Asn Phe
195 200 205

Met Phe Cys Asn Gly Ile Ala Val Ser Gly Asn Met Leu Leu Val Ala
210 215 220

Glu Thr Val Lys Asn Gln Ile Ile Ala Tyr Asp Ile Thr Gly Pro Gly
225 230 235 240

Lys Val Lys Asn Arg Arg Leu Trp Ala Lys Val Pro Lys Pro Ala Gly
245 250 255

Asn Gly Gly Pro Asp Gly Met Asp Phe Asp Glu Thr Gly Arg Leu Leu
260 265 270

Val Ala Asn Tyr Gly Ala Ser His Ile Glu Val Tyr Pro Pro Gly Gly
275 280 285

Ser Gln Glu Pro Ile Val Arg Leu Lys Cys Pro Phe Lys Thr Leu Ser
290 295 300

Asn Leu His Phe Ala Arg Asn Ser Asn Ile Cys Tyr Val Thr Glu His
305 310 315 320

Asp Asn Gly Gly Val Trp Lys Phe Glu Trp Asp Cys Lys Gly Ala Pro
325 330 335

Met Tyr Cys Asp Thr Lys Leu
340

<210> SEQ ID NO 21
<211> LENGTH: 343
<212> TYPE: PRT
<213> ORGANISM: Artificial
<220> FEATURE:
<223> OTHER INFORMATION: CSAV variant

<400> SEQUENCE: 21

Met Ala His His His His His His Val Gly Thr Gly Ser Asn Asp Asp
1 5 10 15

Asp Asp Lys Ser Pro Asp Pro Ala Asp Ser Gly Ile Pro Val Ile Lys
20 25 30

Glu Pro Gln Phe Thr Met Ile Thr Lys Asp Ile Asn Gly Ser Glu Gly
35 40 45

Pro Val Phe Asp Thr Lys Gly Arg Phe Tyr Ala Val Ala Pro Met Glu

```
    50                  55                  60

Ala Ala Asp Glu Asn Arg Glu Pro Gly Gln Phe Thr Asp Gly Ile Ala
65                  70                  75                  80

Gly Lys Leu Tyr Gln Val Asp Leu Asp Ser Gly Val Lys Gln Val Val
                85                  90                  95

Trp Thr Pro His Phe Asp Gly Tyr Gly Gly Arg Pro Ala Gly Cys Gln
            100                 105                 110

Ser Asp His Glu Asp Asn Ile Trp Ile Ala Asp Met Arg Leu Gly Leu
        115                 120                 125

Leu Lys Tyr Asn Val Glu Gly Asn Cys Lys Gln Phe Gly Lys Val Asp
    130                 135                 140

Thr Asp Gly Glu Pro Leu Asn Gly Gly Asn Asp Leu Val Phe Asp Arg
145                 150                 155                 160

Asp Gly Asn Leu Trp Phe Thr Gly Pro Gly Ser Pro Ile Ala Pro Ser
                165                 170                 175

Pro Glu Asp Ile Glu Thr Ile Phe Thr Glu Pro Ser Gly Arg Ile Tyr
            180                 185                 190

Cys Leu Pro Lys Gly Gly Glu Val Pro Ile Lys Val Asp Asp Asn Phe
        195                 200                 205

Met Phe Cys Asn Gly Ile Ala Val Ser Gly Asn Met Leu Leu Val Ala
    210                 215                 220

Glu Thr Val Lys Asn Gln Ile Ile Ala Tyr Asp Ile Thr Gly Pro Gly
225                 230                 235                 240

Lys Val Lys Asn Arg Arg Leu Trp Ala Lys Val Pro Lys Pro Ala Gly
                245                 250                 255

Asn Gly Gly Pro Asp Gly Met Asp Phe Asp Glu Thr Gly Arg Leu Leu
            260                 265                 270

Val Ala Asn Tyr Gly Ala Ser His Ile Glu Val Tyr Pro Pro Gly Gly
        275                 280                 285

Ser Gln Glu Pro Ile Val Arg Leu Lys Cys Pro Phe Lys Thr Leu Ser
    290                 295                 300

Asn Leu His Phe Ala Arg Asn Ser Asn Ile Cys Tyr Val Thr Glu His
305                 310                 315                 320

Asp Asn Gly Gly Val Trp Lys Phe Glu Trp Asp Cys Lys Gly Ala Pro
                325                 330                 335

Met Tyr Cys Asp Thr Lys Leu
            340


<210> SEQ ID NO 22
<211> LENGTH: 343
<212> TYPE: PRT
<213> ORGANISM: Artificial
<220> FEATURE:
<223> OTHER INFORMATION: CSAV variant

<400> SEQUENCE: 22

Met Ala His His His His His His Val Gly Thr Gly Ser Asn Asp Asp
1               5                   10                  15

Asp Asp Lys Ser Pro Asp Pro Ala Asp Ser Gly Ile Pro Val Ile Lys
            20                  25                  30

Glu Pro Gln Phe Thr Met Ile Thr Lys Asp Ile Asn Gly Ser Glu Gly
        35                  40                  45

Pro Val Phe Asp Thr Lys Gly Arg Phe Tyr Ala Val Ala Pro Met Glu
    50                  55                  60

Ala Ala Asp Glu Asn Arg Glu Pro Gly Gln Phe Thr Asp Gly Ile Ala
```

```
65                  70                  75                  80

Gly Lys Leu Tyr Gln Val Asp Leu Asp Ser Gly Val Lys Gln Val Val
                85                  90                  95

Trp Thr Pro His Phe Asp Gly Tyr Gly Gly Arg Pro Ala Gly Cys Gln
            100                 105                 110

Ser Asp His Glu Asp Asn Ile Trp Ile Ala Asp Met Arg Leu Gly Leu
        115                 120                 125

Leu Lys Tyr Asn Val Glu Gly Asn Cys Lys Gln Phe Gly Lys Val Asp
    130                 135                 140

Thr Asp Gly Glu Pro Leu Asn Gly Gly Asn Asp Leu Val Phe Asp Arg
145                 150                 155                 160

Asp Gly Asn Leu Trp Phe Thr Gly Pro Gly Ser Pro Ile Ala Pro Ser
                165                 170                 175

Pro Glu Asp Leu Glu Thr Ile Phe Thr Glu Pro Ser Gly Arg Ile Tyr
            180                 185                 190

Cys Leu Pro Lys Gly Gly Glu Val Pro Ile Lys Val Asp Asp Asn Phe
        195                 200                 205

Met Phe Cys Asn Gly Ile Ala Val Ser Gly Asn Met Leu Leu Val Ala
    210                 215                 220

Glu Thr Val Lys Asn Gln Ile Ile Ala Tyr Asp Ile Thr Gly Pro Gly
225                 230                 235                 240

Lys Val Lys Asn Arg Arg Leu Trp Ala Lys Val Pro Lys Pro Ala Gly
                245                 250                 255

Asn Gly Gly Pro Asp Gly Met Asp Phe Asp Glu Thr Gly Arg Leu Leu
            260                 265                 270

Val Ala Asn Tyr Gly Ala Ser His Ile Glu Val Tyr Pro Pro Gly Gly
        275                 280                 285

Ser Gln Glu Pro Ile Val Arg Leu Lys Cys Pro Phe Lys Thr Leu Ser
    290                 295                 300

Asn Leu His Phe Ala Arg Asn Ser Asn Ile Cys Tyr Val Thr Glu His
305                 310                 315                 320

Asp Asn Gly Gly Val Trp Lys Phe Glu Trp Asp Cys Lys Gly Ala Pro
                325                 330                 335

Met Tyr Cys Asp Thr Lys Leu
            340


<210> SEQ ID NO 23
<211> LENGTH: 343
<212> TYPE: PRT
<213> ORGANISM: Artificial
<220> FEATURE:
<223> OTHER INFORMATION: CSAV variant

<400> SEQUENCE: 23

Met Ala His His His His His His Val Gly Thr Gly Ser Asn Asp Asp
1               5                   10                  15

Asp Asp Lys Ser Pro Asp Pro Ala Asp Ser Gly Ile Pro Val Ile Lys
            20                  25                  30

Glu Pro Gln Phe Thr Met Ile Thr Lys Asp Ile Asn Gly Ser Glu Gly
        35                  40                  45

Pro Val Phe Asp Thr Lys Gly Arg Phe Tyr Ala Val Ala Pro Met Glu
    50                  55                  60

Ala Ala Asp Glu Asn Arg Glu Pro Gly Gln Phe Thr Asp Gly Ile Ala
65                  70                  75                  80

Gly Lys Leu Tyr Gln Val Asp Leu Asp Ser Gly Val Lys Gln Val Val
```

```
                85                  90                  95

Trp Thr Pro His Phe Asp Gly Tyr Gly Gly Arg Pro Ala Gly Cys Gln
            100                 105                 110

Ser Asp His Glu Asp Asn Ile Trp Ile Ala Asp Met Arg Leu Gly Leu
        115                 120                 125

Leu Lys Tyr Asn Val Glu Gly Asn Cys Lys Gln Phe Gly Lys Val Asp
    130                 135                 140

Thr Asp Gly Glu Pro Leu Asn Gly Gly Asn Asp Leu Val Phe Asp Arg
145                 150                 155                 160

Asp Gly Asn Leu Trp Phe Thr Gly Pro Gly Ser Pro Ile Ala Pro Ser
                165                 170                 175

Pro Glu Asp Val Glu Thr Ile Phe Thr Glu Pro Ser Gly Arg Ile Tyr
            180                 185                 190

Cys Leu Pro Lys Gly Gly Glu Val Pro Ile Lys Val Asp Asp Asn Phe
        195                 200                 205

Met Phe Cys Asn Gly Ile Ala Val Ser Gly Asn Met Leu Leu Val Ala
    210                 215                 220

Glu Thr Val Lys Asn Gln Ile Ile Ala Tyr Asp Ile Thr Gly Pro Gly
225                 230                 235                 240

Lys Val Lys Asn Arg Arg Leu Trp Ala Lys Val Pro Lys Pro Ala Gly
                245                 250                 255

Asn Gly Gly Pro Asp Gly Met Asp Phe Asp Glu Thr Gly Arg Leu Leu
            260                 265                 270

Val Ala Asn Tyr Gly Ala Ser His Ile Glu Val Tyr Pro Pro Gly Gly
        275                 280                 285

Ser Gln Glu Pro Ile Val Arg Leu Lys Cys Pro Phe Lys Thr Leu Ser
    290                 295                 300

Asn Leu His Phe Ala Arg Asn Ser Asn Ile Cys Tyr Val Thr Glu His
305                 310                 315                 320

Asp Asn Gly Gly Val Trp Lys Phe Glu Trp Asp Cys Lys Gly Ala Pro
                325                 330                 335

Met Tyr Cys Asp Thr Lys Leu
            340


<210> SEQ ID NO 24
<211> LENGTH: 343
<212> TYPE: PRT
<213> ORGANISM: Artificial
<220> FEATURE:
<223> OTHER INFORMATION: CSAV variant

<400> SEQUENCE: 24

Met Ala His His His His His His Val Gly Thr Gly Ser Asn Asp Asp
1               5                   10                  15

Asp Asp Lys Ser Pro Asp Pro Ala Asp Ser Gly Ile Pro Val Ile Lys
            20                  25                  30

Glu Pro Gln Phe Thr Met Ile Thr Lys Asp Ile Asn Gly Ser Glu Gly
        35                  40                  45

Pro Val Phe Asp Thr Lys Gly Arg Phe Tyr Ala Val Ala Pro Met Glu
    50                  55                  60

Ala Ala Asp Glu Asn Arg Glu Pro Gly Gln Phe Thr Asp Gly Ile Ala
65                  70                  75                  80

Gly Lys Leu Tyr Gln Val Asp Leu Asp Ser Gly Val Lys Gln Val Val
                85                  90                  95

Trp Thr Pro His Phe Asp Gly Tyr Gly Gly Arg Pro Ala Gly Cys Gln
```

```
            100                 105                 110

Ser Asp His Glu Asp Asn Ile Trp Ile Ala Asp Met Arg Leu Gly Leu
        115                 120                 125

Leu Lys Tyr Asn Val Glu Gly Asn Cys Lys Gln Phe Gly Lys Val Asp
    130                 135                 140

Thr Asp Gly Glu Pro Leu Asn Gly Gly Asn Asp Leu Val Phe Asp Arg
145                 150                 155                 160

Asp Gly Asn Leu Trp Phe Thr Gly Pro Gly Ser Pro Ile Ala Pro Ser
                165                 170                 175

Pro Glu Asp Met Glu Thr Ile Phe Thr Glu Pro Ser Gly Arg Ile Tyr
            180                 185                 190

Cys Leu Pro Lys Gly Gly Glu Val Pro Ile Lys Val Asp Asp Asn Phe
        195                 200                 205

Met Phe Cys Asn Gly Ile Ala Val Ser Gly Asn Met Leu Leu Val Ala
    210                 215                 220

Glu Thr Val Lys Asn Gln Ile Ile Ala Tyr Asp Ile Thr Gly Pro Gly
225                 230                 235                 240

Lys Val Lys Asn Arg Arg Leu Trp Ala Lys Val Pro Lys Pro Ala Gly
                245                 250                 255

Asn Gly Gly Pro Asp Gly Met Asp Phe Asp Glu Thr Gly Arg Leu Leu
            260                 265                 270

Val Ala Asn Tyr Gly Ala Ser His Ile Glu Val Tyr Pro Pro Gly Gly
        275                 280                 285

Ser Gln Glu Pro Ile Val Arg Leu Lys Cys Pro Phe Lys Thr Leu Ser
    290                 295                 300

Asn Leu His Phe Ala Arg Asn Ser Asn Ile Cys Tyr Val Thr Glu His
305                 310                 315                 320

Asp Asn Gly Gly Val Trp Lys Phe Glu Trp Asp Cys Lys Gly Ala Pro
                325                 330                 335

Met Tyr Cys Asp Thr Lys Leu
            340


<210> SEQ ID NO 25
<211> LENGTH: 343
<212> TYPE: PRT
<213> ORGANISM: Artificial
<220> FEATURE:
<223> OTHER INFORMATION: CSAV variant

<400> SEQUENCE: 25

Met Ala His His His His His His Val Gly Thr Gly Ser Asn Asp Asp
1               5                   10                  15

Asp Asp Lys Ser Pro Asp Pro Ala Asp Ser Gly Ile Pro Val Ile Lys
            20                  25                  30

Glu Pro Gln Phe Thr Met Ile Thr Lys Asp Ile Asn Gly Ser Glu Gly
        35                  40                  45

Pro Val Phe Asp Thr Lys Gly Arg Phe Tyr Ala Val Ala Pro Met Glu
    50                  55                  60

Ala Ala Asp Glu Asn Arg Glu Pro Gly Gln Phe Thr Asp Gly Ile Ala
65                  70                  75                  80

Gly Lys Leu Tyr Gln Val Asp Leu Asp Ser Gly Val Lys Gln Val Val
                85                  90                  95

Trp Thr Pro His Phe Asp Gly Tyr Gly Gly Arg Pro Ala Gly Cys Gln
            100                 105                 110

Ser Asp His Glu Asp Asn Ile Trp Ile Ala Asp Met Arg Leu Gly Leu
```

```
        115                 120                 125

Leu Lys Tyr Asn Val Glu Gly Asn Cys Lys Gln Phe Gly Lys Val Asp
    130                 135                 140

Thr Asp Gly Glu Pro Leu Asn Gly Gly Asn Asp Leu Val Phe Asp Arg
145                 150                 155                 160

Asp Gly Asn Leu Trp Phe Thr Gly Pro Gly Ser Pro Ile Ala Pro Ser
                165                 170                 175

Pro Glu Asp Arg Glu Thr Ile Phe Thr Glu Pro Ser Gly Arg Ile Tyr
            180                 185                 190

Cys Leu Pro Lys Gly Gly Glu Val Pro Ile Lys Val Asp Asp Asn Phe
        195                 200                 205

Met Phe Cys Asn Gly Ile Ala Val Ser Gly Asn Met Leu Leu Val Ala
    210                 215                 220

Glu Thr Val Lys Asn Gln Ile Ile Ala Tyr Asp Ile Thr Gly Pro Gly
225                 230                 235                 240

Lys Val Lys Asn Arg Arg Leu Trp Ala Lys Val Pro Lys Pro Ala Gly
                245                 250                 255

Asn Gly Gly Pro Asp Gly Met Asp Phe Asp Glu Thr Gly Arg Leu Leu
            260                 265                 270

Val Ala Asn His Gly Ala Ser His Ile Glu Val Tyr Pro Pro Gly Gly
        275                 280                 285

Ser Gln Glu Pro Ile Val Arg Leu Lys Cys Pro Phe Lys Thr Leu Ser
    290                 295                 300

Asn Leu His Phe Ala Arg Asn Ser Asn Ile Cys Tyr Val Thr Glu His
305                 310                 315                 320

Asp Asn Gly Gly Val Trp Lys Phe Glu Trp Asp Cys Lys Gly Ala Pro
                325                 330                 335

Met Tyr Cys Asp Thr Lys Leu
            340


<210> SEQ ID NO 26
<211> LENGTH: 343
<212> TYPE: PRT
<213> ORGANISM: Artificial
<220> FEATURE:
<223> OTHER INFORMATION: CSAV variant

<400> SEQUENCE: 26

Met Ala His His His His His His Val Gly Thr Gly Ser Asn Asp Asp
1               5                   10                  15

Asp Asp Lys Ser Pro Asp Pro Ala Asp Ser Gly Ile Pro Val Ile Lys
            20                  25                  30

Glu Pro Gln Phe Thr Met Ile Thr Lys Asp Ile Asn Gly Ser Glu Gly
        35                  40                  45

Pro Val Phe Asp Thr Lys Gly Arg Phe Tyr Ala Val Ala Pro Met Glu
    50                  55                  60

Ala Ala Asp Glu Asn Arg Glu Pro Gly Gln Phe Thr Asp Gly Ile Ala
65                  70                  75                  80

Gly Lys Leu Tyr Gln Val Asp Leu Asp Ser Gly Val Lys Gln Val Val
                85                  90                  95

Trp Thr Pro His Phe Asp Gly Tyr Gly Gly Arg Pro Ala Gly Cys Gln
            100                 105                 110

Ser Asp His Glu Asp Asn Ile Trp Ile Ala Asp Met Arg Leu Gly Leu
        115                 120                 125

Leu Lys Tyr Asn Val Glu Gly Asn Cys Lys Gln Phe Gly Lys Val Asp
```

```
    130                 135                 140

Thr Asp Gly Glu Pro Leu Asn Gly Gly Asn Asp Leu Val Phe Asp Arg
145                 150                 155                 160

Asp Gly Asn Leu Trp Phe Thr Gly Pro Gly Ser Pro Ile Ala Pro Ser
                165                 170                 175

Pro Glu Asp Arg Glu Thr Ile Phe Thr Glu Pro Ser Gly Arg Ile Tyr
            180                 185                 190

Cys Leu Pro Lys Gly Gly Glu Val Pro Ile Lys Val Asp Asp Asn Phe
        195                 200                 205

Met Phe Cys Asn Gly Ile Ala Val Ser Gly Asn Met Leu Leu Val Ala
    210                 215                 220

Glu Thr Val Lys Asn Gln Ile Ile Ala Tyr Asp Ile Thr Gly Pro Gly
225                 230                 235                 240

Lys Val Lys Asn Arg Arg Leu Trp Ala Lys Val Pro Lys Pro Ala Gly
                245                 250                 255

Asn Gly Gly Pro Asp Gly Met Asp Phe Asp Glu Thr Gly Arg Leu Leu
            260                 265                 270

Val Ala Asn Phe Gly Ala Ser His Ile Glu Val Tyr Pro Pro Gly Gly
        275                 280                 285

Ser Gln Glu Pro Ile Val Arg Leu Lys Cys Pro Phe Lys Thr Leu Ser
    290                 295                 300

Asn Leu His Phe Ala Arg Asn Ser Asn Ile Cys Tyr Val Thr Glu His
305                 310                 315                 320

Asp Asn Gly Gly Val Trp Lys Phe Glu Trp Asp Cys Lys Gly Ala Pro
                325                 330                 335

Met Tyr Cys Asp Thr Lys Leu
            340


<210> SEQ ID NO 27
<211> LENGTH: 336
<212> TYPE: PRT
<213> ORGANISM: Artificial
<220> FEATURE:
<223> OTHER INFORMATION: CINT variant

<400> SEQUENCE: 27

Met Ala His His His His His His Val Gly Thr Gly Ser Asn Asp Asp
1               5                   10                  15

Asp Asp Lys Ser Pro Asp Pro Ala Lys Thr Ile Glu Pro Lys Phe Lys
            20                  25                  30

Met Val Thr Lys Asp Ile Asp Gly Ser Glu Gly Pro Val Phe Asp Thr
        35                  40                  45

Lys Gly Arg Phe Tyr Ala Val Ala Pro Met Glu Ser Ala Asp Asp Asn
    50                  55                  60

Arg Glu Thr Gly Gln Phe Leu Asp Gly Ile Ala Gly Lys Leu Tyr Ser
65                  70                  75                  80

Val Asn Leu Asn Thr Gly Glu Lys Gln Val Val Cys Thr Pro Gln Phe
                85                  90                  95

Asn Gly Tyr Gly Gly Arg Pro Ala Gly Cys Gln Ser Asp Lys Glu Asp
            100                 105                 110

Asn Ile Trp Ile Ala Asp Met Arg Leu Gly Leu Leu Lys Tyr Asp Gly
        115                 120                 125

Lys Gly Asn Cys Lys Gln Phe Ser Val Val Asp Thr Asp Gly Asn Pro
    130                 135                 140

Leu Asn Gly Ala Asn Asp Leu Val Phe Asp Asp Asp Gly Asn Leu Trp
```

```
145                 150                 155                 160

Phe Thr Gly Pro Gly Ser Pro Val Ala Pro Ser Val Phe Asp Arg Thr
                165                 170                 175

Thr Ile Phe Ala Glu Pro Thr Gly Arg Ile Tyr Cys Leu Pro Lys Gly
            180                 185                 190

Ser Glu Val Pro Ile Lys Val Asp Asp Asn Phe Arg Phe Cys Asn Gly
        195                 200                 205

Ile Ala Val Thr Gly Lys Leu Leu Leu Val Ala Glu Thr Met Thr Lys
    210                 215                 220

Gln Ile Ile Ala Tyr Asp Val Thr Gly Pro Gly Asn Val Thr Asn Arg
225                 230                 235                 240

Arg Ile Trp Ser Lys Val Pro Lys Gly Ala Glu Gln Gly Gly Pro Asp
                245                 250                 255

Gly Met Asp Phe Asp Glu Arg Gly Cys Leu Leu Val Ala Asn His Gly
            260                 265                 270

Gly Ser His Ile Glu Val Tyr Pro Pro Glu Gly Gly Asp Glu Pro Ile
        275                 280                 285

Ile Arg Val Arg Cys Pro Phe Lys Thr Pro Ser Asn Val His Phe Ala
    290                 295                 300

Gln Asn Ser Asn Val Cys Tyr Val Thr Glu His Asp Thr Asn Gly Val
305                 310                 315                 320

Trp Ala Phe Glu Trp Asp Cys Lys Gly Ala Leu Met Tyr Cys Asp Lys
                325                 330                 335


<210> SEQ ID NO 28
<211> LENGTH: 336
<212> TYPE: PRT
<213> ORGANISM: Artificial
<220> FEATURE:
<223> OTHER INFORMATION: CINT variant

<400> SEQUENCE: 28

Met Ala His His His His His His Val Gly Thr Gly Ser Asn Asp Asp
1               5                   10                  15

Asp Asp Lys Ser Pro Asp Pro Ala Lys Thr Ile Glu Pro Lys Phe Lys
            20                  25                  30

Met Val Thr Lys Asp Ile Asp Gly Ser Glu Gly Pro Val Phe Asp Thr
        35                  40                  45

Lys Gly Arg Phe Tyr Ala Val Ala Pro Met Glu Ser Ala Asp Asp Asn
    50                  55                  60

Arg Glu Thr Gly Gln Phe Leu Asp Gly Ile Ala Gly Lys Leu Tyr Ser
65                  70                  75                  80

Val Asn Leu Asn Thr Gly Glu Lys Gln Val Val Cys Thr Pro Gln Phe
                85                  90                  95

Asn Gly Tyr Gly Gly Arg Pro Ala Gly Cys Gln Ser Asp Lys Glu Asp
            100                 105                 110

Asn Ile Trp Ile Ala Asp Met Arg Leu Gly Leu Leu Lys Tyr Asp Gly
        115                 120                 125

Lys Gly Asn Cys Lys Gln Phe Ser Val Val Asp Thr Asp Gly Asn Pro
    130                 135                 140

Leu Asn Gly Ala Asn Asp Leu Val Phe Asp Asp Asp Gly Asn Leu Trp
145                 150                 155                 160

Phe Thr Gly Pro Gly Ser Pro Val Ala Pro Ser Val Val Asp Arg Thr
                165                 170                 175

Thr Ile Phe Ala Glu Pro Thr Gly Arg Ile Tyr Cys Leu Pro Lys Gly
```

```
            180                 185                 190

Ser Glu Val Pro Ile Lys Val Asp Asp Asn Phe Arg Phe Cys Asn Gly
        195                 200                 205

Ile Ala Val Thr Gly Lys Leu Leu Leu Val Ala Glu Thr Met Thr Lys
    210                 215                 220

Gln Ile Ile Ala Tyr Asp Val Thr Gly Pro Gly Asn Val Thr Asn Arg
225                 230                 235                 240

Arg Ile Trp Ser Lys Val Pro Lys Gly Ala Glu Gln Gly Gly Pro Asp
                245                 250                 255

Gly Met Asp Phe Asp Glu Arg Gly Cys Leu Leu Val Ala Asn His Gly
            260                 265                 270

Gly Ser His Ile Glu Val Tyr Pro Pro Glu Gly Gly Asp Glu Pro Ile
        275                 280                 285

Ile Arg Val Arg Cys Pro Phe Lys Thr Pro Ser Asn Val His Phe Ala
    290                 295                 300

Gln Asn Ser Asn Val Cys Tyr Val Thr Glu His Asp Thr Asn Gly Val
305                 310                 315                 320

Trp Ala Phe Glu Trp Asp Cys Lys Gly Ala Leu Met Tyr Cys Asp Lys
                325                 330                 335


<210> SEQ ID NO 29
<211> LENGTH: 336
<212> TYPE: PRT
<213> ORGANISM: Artificial
<220> FEATURE:
<223> OTHER INFORMATION: CINT variant

<400> SEQUENCE: 29

Met Ala His His His His His His Val Gly Thr Gly Ser Asn Asp Asp
1               5                   10                  15

Asp Asp Lys Ser Pro Asp Pro Ala Lys Thr Ile Glu Pro Lys Phe Lys
            20                  25                  30

Met Val Thr Lys Asp Ile Asp Gly Ser Glu Gly Pro Val Phe Asp Thr
        35                  40                  45

Lys Gly Arg Phe Tyr Ala Val Ala Pro Met Glu Ser Ala Asp Asp Asn
    50                  55                  60

Arg Glu Thr Gly Gln Phe Leu Asp Gly Ile Ala Gly Lys Leu Tyr Ser
65                  70                  75                  80

Val Asn Leu Asn Thr Gly Glu Lys Gln Val Val Cys Thr Pro Gln Phe
                85                  90                  95

Asn Gly Tyr Gly Gly Arg Pro Ala Gly Cys Gln Ser Asp Lys Glu Asp
            100                 105                 110

Asn Ile Trp Ile Ala Asp Met Arg Leu Gly Leu Leu Lys Tyr Asp Gly
        115                 120                 125

Lys Gly Asn Cys Lys Gln Phe Ser Val Val Asp Thr Asp Gly Asn Pro
    130                 135                 140

Leu Asn Gly Ala Asn Asp Leu Val Phe Asp Asp Asp Gly Asn Leu Trp
145                 150                 155                 160

Phe Thr Gly Pro Gly Ser Pro Val Ala Pro Ser Val Glu Asp Ala Thr
                165                 170                 175

Thr Ile Phe Ala Glu Pro Thr Gly Arg Ile Tyr Cys Leu Pro Lys Gly
            180                 185                 190

Ser Glu Val Pro Ile Lys Val Asp Asp Asn Phe Arg Phe Cys Asn Gly
        195                 200                 205

Ile Ala Val Thr Gly Lys Leu Leu Leu Val Ala Glu Thr Met Thr Lys
```

```
    210                 215                 220

Gln Ile Ile Ala Tyr Asp Val Thr Gly Pro Gly Asn Val Thr Asn Arg
225                 230                 235                 240

Arg Ile Trp Ser Lys Val Pro Lys Gly Ala Glu Gln Gly Gly Pro Asp
                245                 250                 255

Gly Met Asp Phe Asp Glu Arg Gly Cys Leu Leu Val Ala Asn His Gly
            260                 265                 270

Gly Ser His Ile Glu Val Tyr Pro Pro Glu Gly Gly Asp Glu Pro Ile
        275                 280                 285

Ile Arg Val Arg Cys Pro Phe Lys Thr Pro Ser Asn Val His Phe Ala
    290                 295                 300

Gln Asn Ser Asn Val Cys Tyr Val Thr Glu His Asp Thr Asn Gly Val
305                 310                 315                 320

Trp Ala Phe Glu Trp Asp Cys Lys Gly Ala Leu Met Tyr Cys Asp Lys
                325                 330                 335


<210> SEQ ID NO 30
<211> LENGTH: 336
<212> TYPE: PRT
<213> ORGANISM: Artificial
<220> FEATURE:
<223> OTHER INFORMATION: CINT variant

<400> SEQUENCE: 30

Met Ala His His His His His His Val Gly Thr Gly Ser Asn Asp Asp
1               5                   10                  15

Asp Asp Lys Ser Pro Asp Pro Ala Lys Thr Ile Glu Pro Lys Phe Lys
            20                  25                  30

Met Val Thr Lys Asp Ile Asp Gly Ser Glu Gly Pro Val Phe Asp Thr
        35                  40                  45

Lys Gly Arg Phe Tyr Ala Val Ala Pro Met Glu Leu Ala Asp Asp Asn
    50                  55                  60

Arg Glu Thr Gly Gln Phe Leu Asp Gly Ile Ala Gly Lys Leu Tyr Ser
65                  70                  75                  80

Val Asn Leu Asn Thr Gly Glu Lys Gln Val Val Cys Thr Pro Gln Phe
                85                  90                  95

Asn Gly Tyr Gly Gly Arg Pro Ala Gly Cys Gln Ser Asp Lys Glu Asp
            100                 105                 110

Asn Ile Trp Ile Ala Asp Met Arg Leu Gly Leu Leu Lys Tyr Asp Gly
        115                 120                 125

Lys Gly Asn Cys Lys Gln Phe Ser Val Val Asp Thr Asp Gly Asn Pro
    130                 135                 140

Leu Asn Gly Ala Asn Asp Leu Val Phe Asp Asp Asp Gly Asn Leu Trp
145                 150                 155                 160

Phe Thr Gly Pro Gly Ser Pro Val Ala Pro Ser Val Glu Asp Arg Thr
                165                 170                 175

Thr Ile Phe Ala Glu Pro Thr Gly Arg Ile Tyr Cys Leu Pro Lys Gly
            180                 185                 190

Ser Glu Val Pro Ile Lys Val Asp Asp Asn Phe Arg Phe Cys Asn Gly
        195                 200                 205

Ile Ala Val Thr Gly Lys Leu Leu Leu Val Ala Glu Thr Met Thr Lys
    210                 215                 220

Gln Ile Ile Ala Tyr Asp Val Thr Gly Pro Gly Asn Val Thr Asn Arg
225                 230                 235                 240

Arg Ile Trp Ser Lys Val Pro Lys Gly Ala Glu Gln Gly Gly Pro Asp
```

```
                245                 250                 255

Gly Met Asp Phe Asp Glu Arg Gly Cys Leu Leu Val Ala Asn His Gly
            260                 265                 270

Gly Ser His Ile Glu Val Tyr Pro Pro Glu Gly Gly Asp Glu Pro Ile
        275                 280                 285

Ile Arg Val Arg Cys Pro Phe Lys Thr Pro Ser Asn Val His Phe Ala
    290                 295                 300

Gln Asn Ser Asn Val Cys Tyr Val Thr Glu His Asp Thr Asn Gly Val
305                 310                 315                 320

Trp Ala Phe Glu Trp Asp Cys Lys Gly Ala Leu Met Tyr Cys Asp Lys
                325                 330                 335


<210> SEQ ID NO 31
<211> LENGTH: 336
<212> TYPE: PRT
<213> ORGANISM: Artificial
<220> FEATURE:
<223> OTHER INFORMATION: CINT variant

<400> SEQUENCE: 31

Met Ala His His His His His His Val Gly Thr Gly Ser Asn Asp Asp
1               5                   10                  15

Asp Asp Lys Ser Pro Asp Pro Ala Lys Thr Ile Glu Pro Lys Phe Lys
            20                  25                  30

Met Val Thr Lys Asp Ile Asp Gly Ser Glu Gly Pro Val Phe Asp Thr
        35                  40                  45

Lys Gly Arg Phe Tyr Ala Val Ala Pro Met Glu Arg Ala Asp Asp Asn
    50                  55                  60

Arg Glu Thr Gly Gln Phe Leu Asp Gly Ile Ala Gly Lys Leu Tyr Ser
65                  70                  75                  80

Val Asn Leu Asn Thr Gly Glu Lys Gln Val Val Cys Thr Pro Gln Phe
                85                  90                  95

Asn Gly Tyr Gly Gly Arg Pro Ala Gly Cys Gln Ser Asp Lys Glu Asp
            100                 105                 110

Asn Ile Trp Ile Ala Asp Met Arg Leu Gly Leu Leu Lys Tyr Asp Gly
        115                 120                 125

Lys Gly Asn Cys Lys Gln Phe Ser Val Val Asp Thr Asp Gly Asn Pro
    130                 135                 140

Leu Asn Gly Ala Asn Asp Leu Val Phe Asp Asp Asp Gly Asn Leu Trp
145                 150                 155                 160

Phe Thr Gly Pro Gly Ser Pro Val Ala Pro Ser Val Glu Asp Arg Thr
                165                 170                 175

Thr Ile Phe Ala Glu Pro Thr Gly Arg Ile Tyr Cys Leu Pro Lys Gly
            180                 185                 190

Ser Glu Val Pro Ile Lys Val Asp Asp Asn Phe Arg Phe Cys Asn Gly
        195                 200                 205

Ile Ala Val Thr Gly Lys Leu Leu Leu Val Ala Glu Thr Met Thr Lys
    210                 215                 220

Gln Ile Ile Ala Tyr Asp Val Thr Gly Pro Gly Asn Val Thr Asn Arg
225                 230                 235                 240

Arg Ile Trp Ser Lys Val Pro Lys Gly Ala Glu Gln Gly Gly Pro Asp
                245                 250                 255

Gly Met Asp Phe Asp Glu Arg Gly Cys Leu Leu Val Ala Asn His Gly
            260                 265                 270

Gly Ser His Ile Glu Val Tyr Pro Pro Glu Gly Gly Asp Glu Pro Ile
```

```
        275                 280                 285

Ile Arg Val Arg Cys Pro Phe Lys Thr Pro Ser Asn Val His Phe Ala
    290                 295                 300

Gln Asn Ser Asn Val Cys Tyr Val Thr Glu His Asp Thr Asn Gly Val
305                 310                 315                 320

Trp Ala Phe Glu Trp Asp Cys Lys Gly Ala Leu Met Tyr Cys Asp Lys
                325                 330                 335


<210> SEQ ID NO 32
<211> LENGTH: 44
<212> TYPE: DNA
<213> ORGANISM: Artificial
<220> FEATURE:
<223> OTHER INFORMATION: Mutagenic primer

<400> SEQUENCE: 32

cggttctcgt ccgcagcctc agcaggcgca accgcataga agcg                      44


<210> SEQ ID NO 33
<211> LENGTH: 44
<212> TYPE: DNA
<213> ORGANISM: Artificial
<220> FEATURE:
<223> OTHER INFORMATION: Mutagenic primer

<400> SEQUENCE: 33

cggttctcgt ccgcagcctc accaggcgca accgcataga agcg                      44


<210> SEQ ID NO 34
<211> LENGTH: 48
<212> TYPE: DNA
<213> ORGANISM: Artificial
<220> FEATURE:
<223> OTHER INFORMATION: Mutagenic primer

<400> SEQUENCE: 34

ggtctgattg acaaccagca gggatacctc catagccgtc aaaatgag                  48


<210> SEQ ID NO 35
<211> LENGTH: 48
<212> TYPE: DNA
<213> ORGANISM: Artificial
<220> FEATURE:
<223> OTHER INFORMATION: Mutagenic primer

<400> SEQUENCE: 35

ggtctgattg acaaccagca ggaacacctc catagccgtc aaaatgag                  48


<210> SEQ ID NO 36
<211> LENGTH: 48
<212> TYPE: DNA
<213> ORGANISM: Artificial
<220> FEATURE:
<223> OTHER INFORMATION: Mutagenic primer

<400> SEQUENCE: 36

ggtctgattg acaaccagca ggaagacctc catagccgtc aaaatgag                  48


<210> SEQ ID NO 37
<211> LENGTH: 46
<212> TYPE: DNA
<213> ORGANISM: Artificial
<220> FEATURE:
<223> OTHER INFORMATION: Mutagenic primer
```

<400> SEQUENCE: 37
cctcatggtc tgattgacaa cctgaagggc gacctccata gccgtc 46

<210> SEQ ID NO 38
<211> LENGTH: 46
<212> TYPE: DNA
<213> ORGANISM: Artificial
<220> FEATURE:
<223> OTHER INFORMATION: Mutagenic primer

<400> SEQUENCE: 38
cctcatggtc tgattgacaa ccacaagggc gacctccata gccgtc 46

<210> SEQ ID NO 39
<211> LENGTH: 48
<212> TYPE: DNA
<213> ORGANISM: Artificial
<220> FEATURE:
<223> OTHER INFORMATION: Mutagenic primer

<400> SEQUENCE: 39
cagtaaagat agtctcgcgg tcaaaaggtg aaggtgcgat aggtgatc 48

<210> SEQ ID NO 40
<211> LENGTH: 48
<212> TYPE: DNA
<213> ORGANISM: Artificial
<220> FEATURE:
<223> OTHER INFORMATION: Mutagenic primer

<400> SEQUENCE: 40
cagtaaagat agtctcgcgg tcgataggtg aaggtgcgat aggtgatc 48

<210> SEQ ID NO 41
<211> LENGTH: 48
<212> TYPE: DNA
<213> ORGANISM: Artificial
<220> FEATURE:
<223> OTHER INFORMATION: Mutagenic primer

<400> SEQUENCE: 41
cagtaaagat agtctcgcgg tcaagaggtg aaggtgcgat aggtgatc 48

<210> SEQ ID NO 42
<211> LENGTH: 48
<212> TYPE: DNA
<213> ORGANISM: Artificial
<220> FEATURE:
<223> OTHER INFORMATION: Mutagenic primer

<400> SEQUENCE: 42
cagtaaagat agtctcgcgg tcaacaggtg aaggtgcgat aggtgatc 48

<210> SEQ ID NO 43
<211> LENGTH: 49
<212> TYPE: DNA
<213> ORGANISM: Artificial
<220> FEATURE:
<223> OTHER INFORMATION: Mutagenic primer

<400> SEQUENCE: 43
gaaggctcag taaagatagt ctcaaagtcc tcaggtgaag gtgcgatag 49

<210> SEQ ID NO 44
<211> LENGTH: 49

<212> TYPE: DNA
<213> ORGANISM: Artificial
<220> FEATURE:
<223> OTHER INFORMATION: Mutagenic primer

<400> SEQUENCE: 44
gaaggctcag taaagatagt ctcgatgtcc tcaggtgaag gtgcgatag 49

<210> SEQ ID NO 45
<211> LENGTH: 49
<212> TYPE: DNA
<213> ORGANISM: Artificial
<220> FEATURE:
<223> OTHER INFORMATION: Mutagenic primer

<400> SEQUENCE: 45
gaaggctcag taaagatagt ctcaaggtcc tcaggtgaag gtgcgatag 49

<210> SEQ ID NO 46
<211> LENGTH: 49
<212> TYPE: DNA
<213> ORGANISM: Artificial
<220> FEATURE:
<223> OTHER INFORMATION: Mutagenic primer

<400> SEQUENCE: 46
gaaggctcag taaagatagt ctcaacgtcc tcaggtgaag gtgcgatag 49

<210> SEQ ID NO 47
<211> LENGTH: 49
<212> TYPE: DNA
<213> ORGANISM: Artificial
<220> FEATURE:
<223> OTHER INFORMATION: Mutagenic primer

<400> SEQUENCE: 47
gaaggctcag taaagatagt ctccatgtcc tcaggtgaag gtgcgatag 49

<210> SEQ ID NO 48
<211> LENGTH: 51
<212> TYPE: DNA
<213> ORGANISM: Artificial
<220> FEATURE:
<223> OTHER INFORMATION: Mutagenic primer

<400> SEQUENCE: 48
gatatacctc gatgtgtgaa gcgccgtggt tagcaacaag aaggcgacca g 51

<210> SEQ ID NO 49
<211> LENGTH: 51
<212> TYPE: DNA
<213> ORGANISM: Artificial
<220> FEATURE:
<223> OTHER INFORMATION: Mutagenic primer

<400> SEQUENCE: 49
gatatacctc gatgtgtgaa gcgccaaagt tagcaacaag aaggcgacca g 51

<210> SEQ ID NO 50
<211> LENGTH: 43
<212> TYPE: DNA
<213> ORGANISM: Artificial
<220> FEATURE:
<223> OTHER INFORMATION: Mutagenic primer

<400> SEQUENCE: 50

-continued

```
gaagatcgtc gtgcggtcga atactgaagg agcaacaggt gag                    43


<210> SEQ ID NO 51
<211> LENGTH: 43
<212> TYPE: DNA
<213> ORGANISM: Artificial
<220> FEATURE:
<223> OTHER INFORMATION: Mutagenic primer

<400> SEQUENCE: 51

gaagatcgtc gtgcggtcaa ctactgaagg agcaacaggt gag                    43


<210> SEQ ID NO 52
<211> LENGTH: 44
<212> TYPE: DNA
<213> ORGANISM: Artificial
<220> FEATURE:
<223> OTHER INFORMATION: Mutagenic primer

<400> SEQUENCE: 52

ctccgcgaag atcgtcgtag cgtcctctac tgaaggagca acag                   44


<210> SEQ ID NO 53
<211> LENGTH: 43
<212> TYPE: DNA
<213> ORGANISM: Artificial
<220> FEATURE:
<223> OTHER INFORMATION: Mutagenic primer

<400> SEQUENCE: 53

ctcgcggttg tcgtcagcaa gctccatagg agctactgca tag                    43


<210> SEQ ID NO 54
<211> LENGTH: 43
<212> TYPE: DNA
<213> ORGANISM: Artificial
<220> FEATURE:
<223> OTHER INFORMATION: Mutagenic primer

<400> SEQUENCE: 54

ctcgcggttg tcgtcagcgc gctccatagg agctactgca tag                    43
```